United States Patent
Sohn et al.

[11] Patent Number: 5,988,171
[45] Date of Patent: Nov. 23, 1999

[54] METHODS AND DEVICES FOR THE TREATMENT OF AIRWAY OBSTRUCTION, SLEEP APNEA AND SNORING

[75] Inventors: Ze'ev Sohn, Modiin; Ari DeRowe, Moshav Salit, both of Israel

[73] Assignee: Influence Medical Technologies, Ltd., Herzelia B., Israel

[21] Appl. No.: 08/883,220

[22] Filed: Jun. 26, 1997

[51] Int. Cl.⁶ .................................................. A61F 5/56
[52] U.S. Cl. .................................... 128/848; 606/232
[58] Field of Search .................................. 128/846, 848; 606/232

[56] References Cited

U.S. PATENT DOCUMENTS

| | | | |
|---|---|---|---|
| 4,676,240 | 6/1987 | Gardy | 128/848 |
| 5,154,184 | 10/1992 | Alvarez | 128/848 |
| 5,316,020 | 5/1994 | Truffer | 128/848 |
| 5,373,859 | 12/1994 | Forney | 128/846 |
| 5,620,012 | 4/1997 | Benderev et al. | 128/898 |

*Primary Examiner*—Gary Jackson
*Attorney, Agent, or Firm*—Levisohn, Lerner, Berger & Langsam

[57] ABSTRACT

Methods and devices for the treatment of airway obstruction, sleep apnea and snoring, by tongue suspension for treatment of airway obstruction in a human subject, including the steps of inserting a bone anchor into the mandible of the subject, and fastening at least one suture to the bone anchor to suspend the tongue to the mandible. Preferably, the bone anchors used are surgical screws. The sutures are fastened to at least one surgical screw, and are preferably inserted in positions adjacent to the mandible's midline. Alternatively, suspension of the hyoid bone is accomplished.

57 Claims, 24 Drawing Sheets

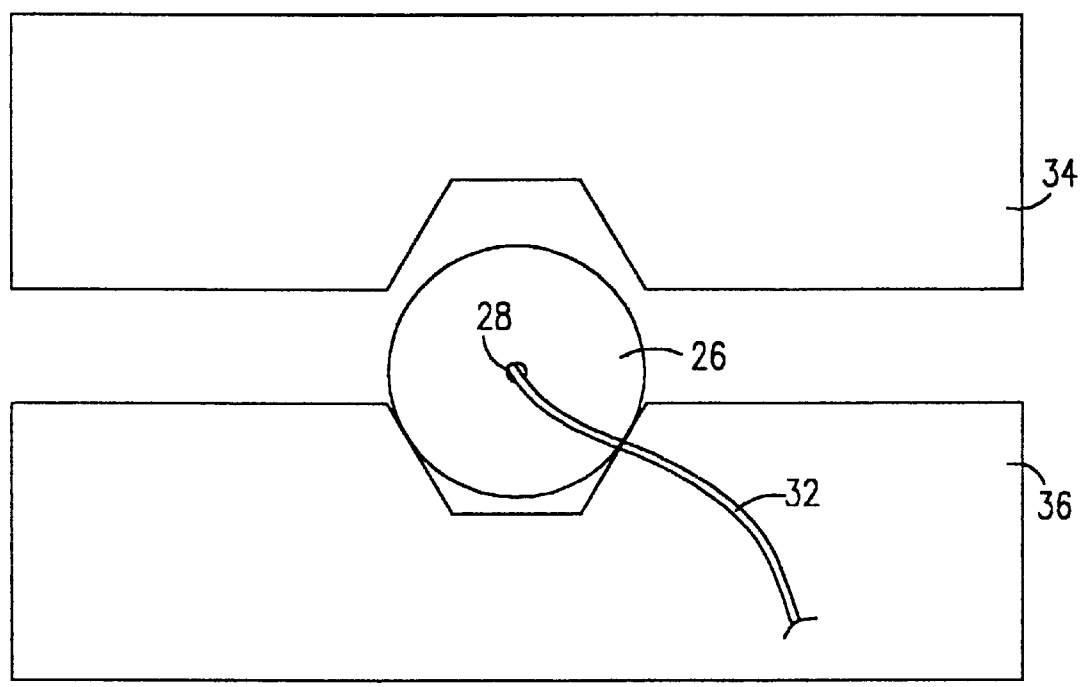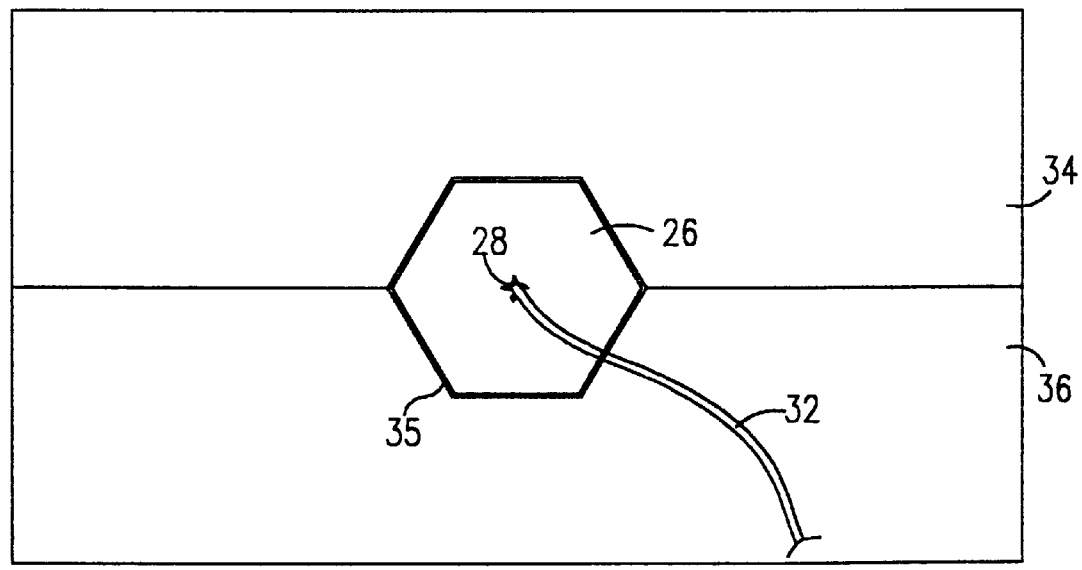

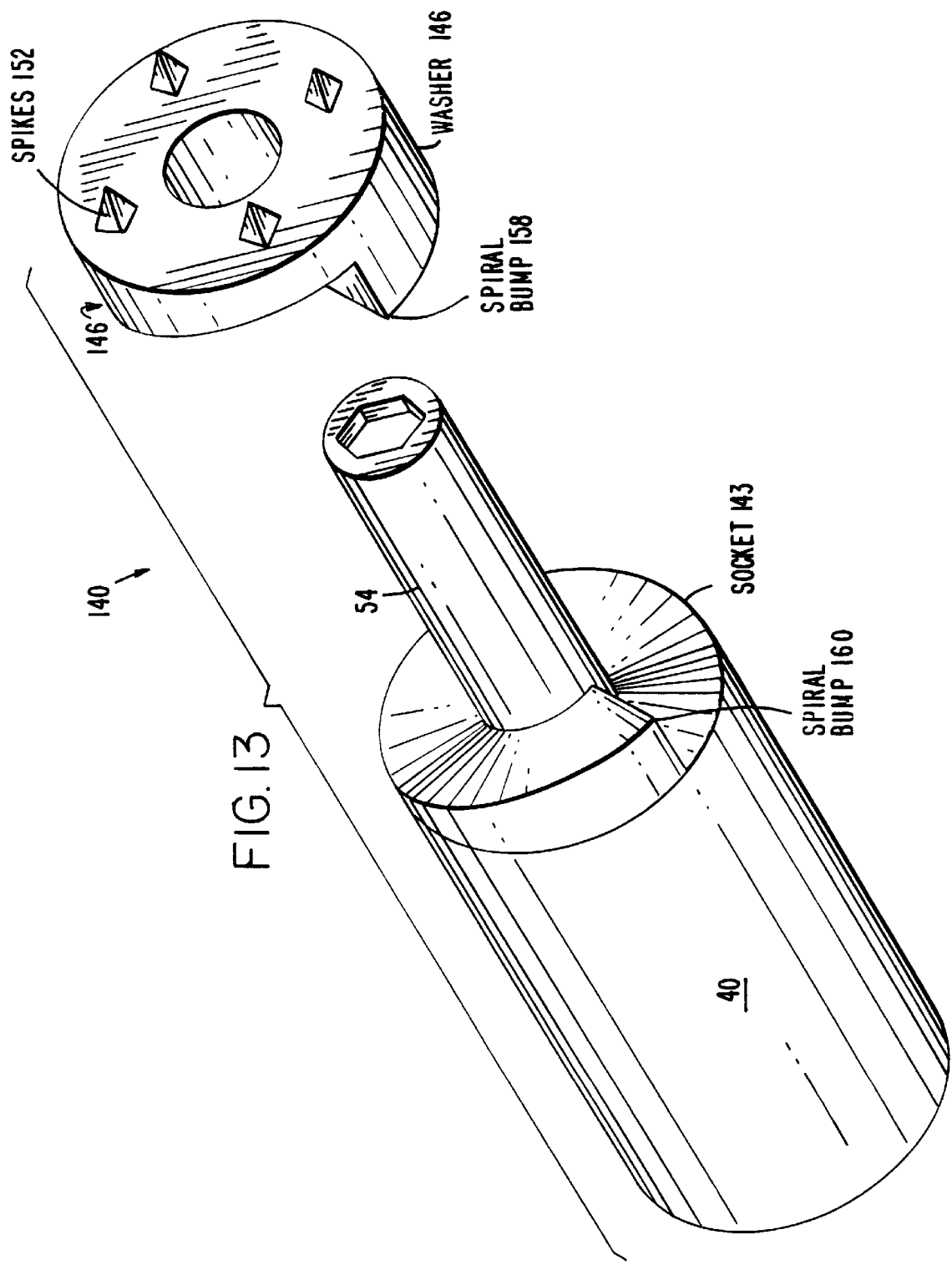

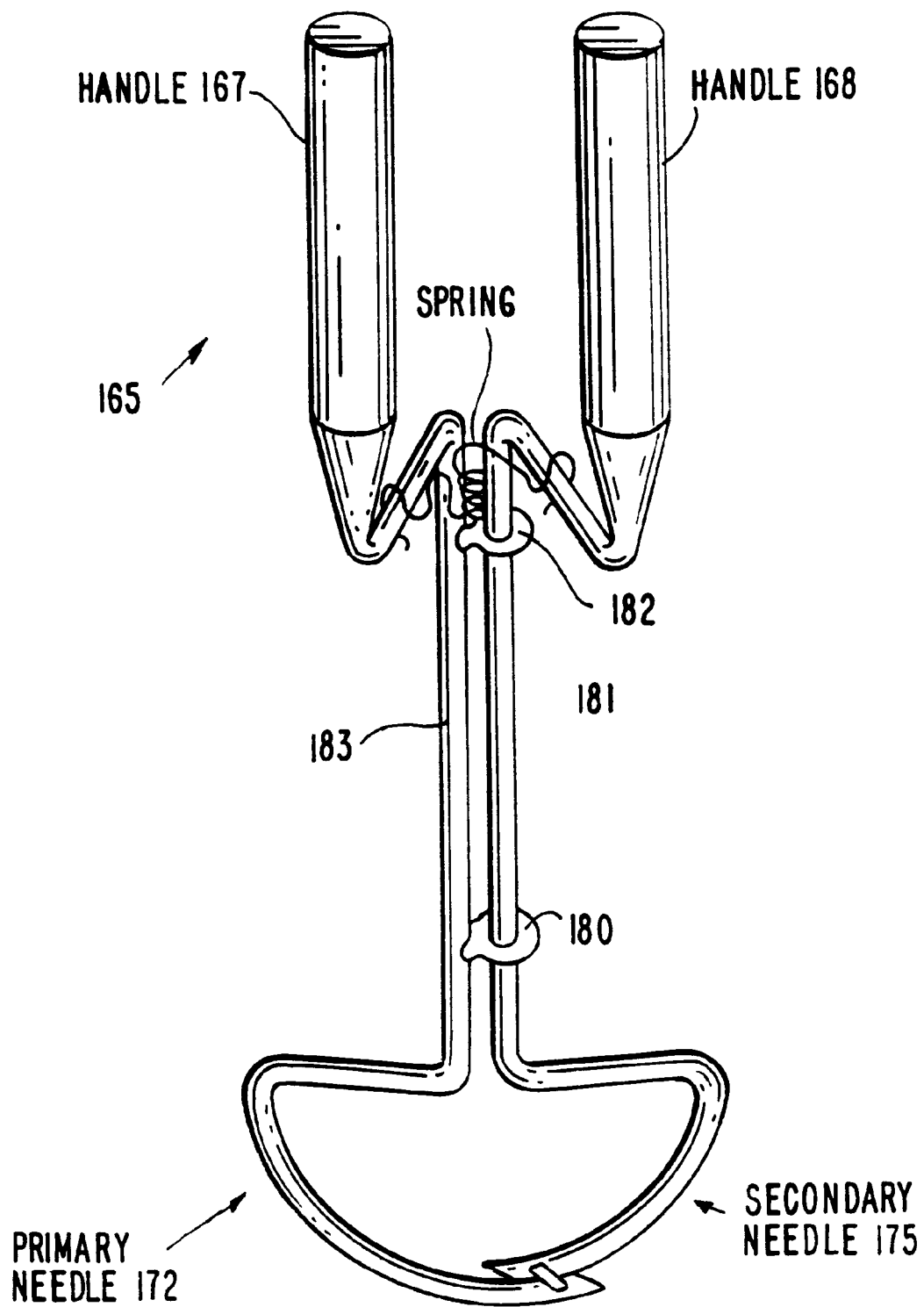

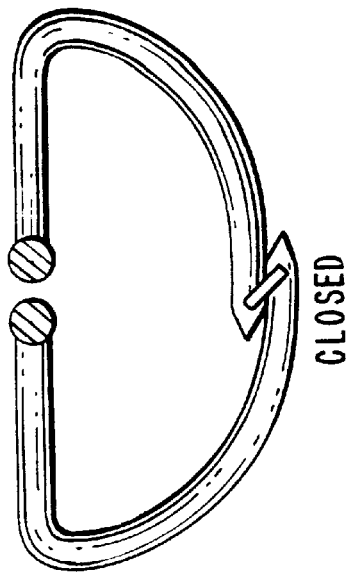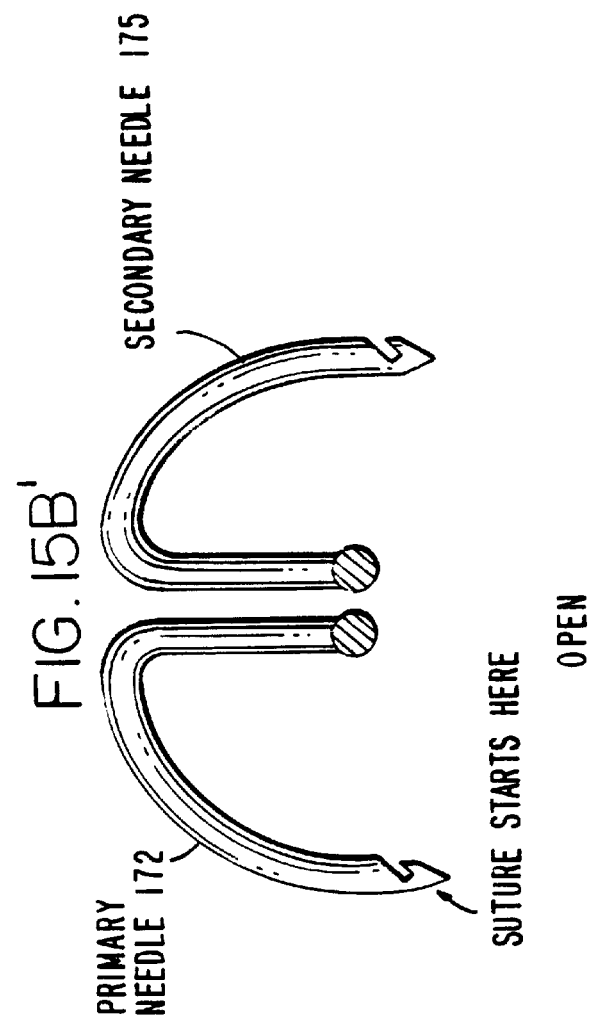

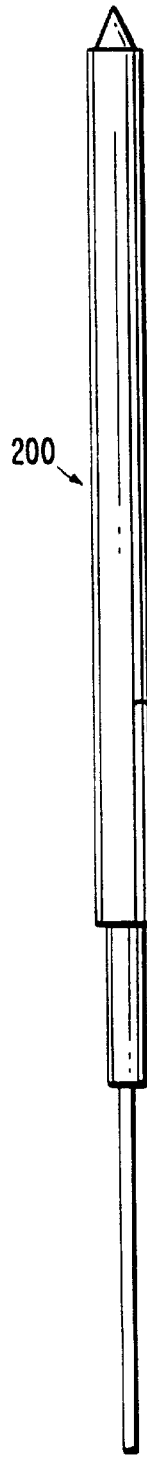
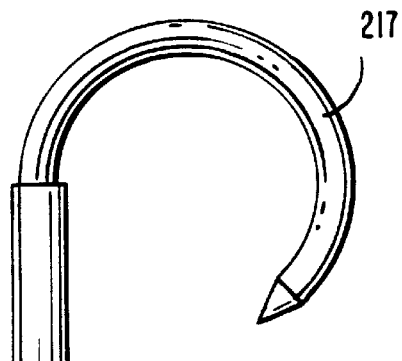
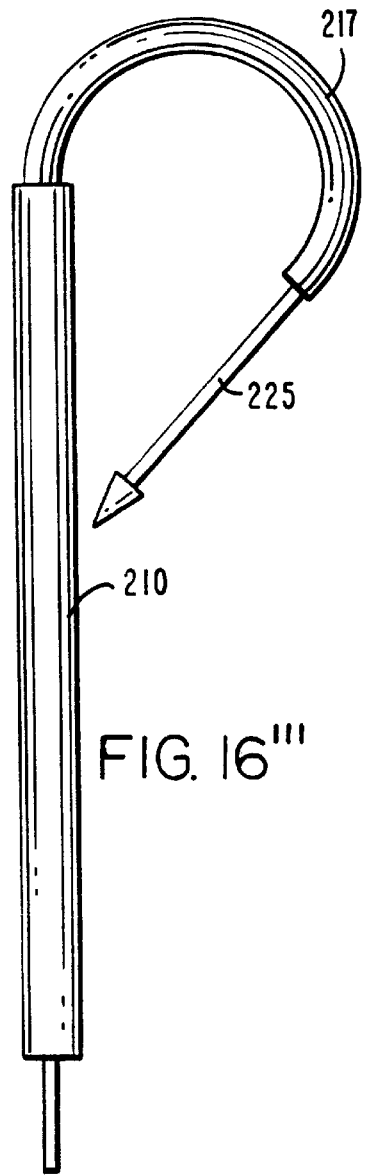

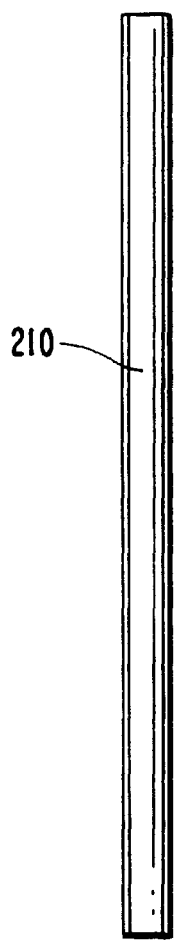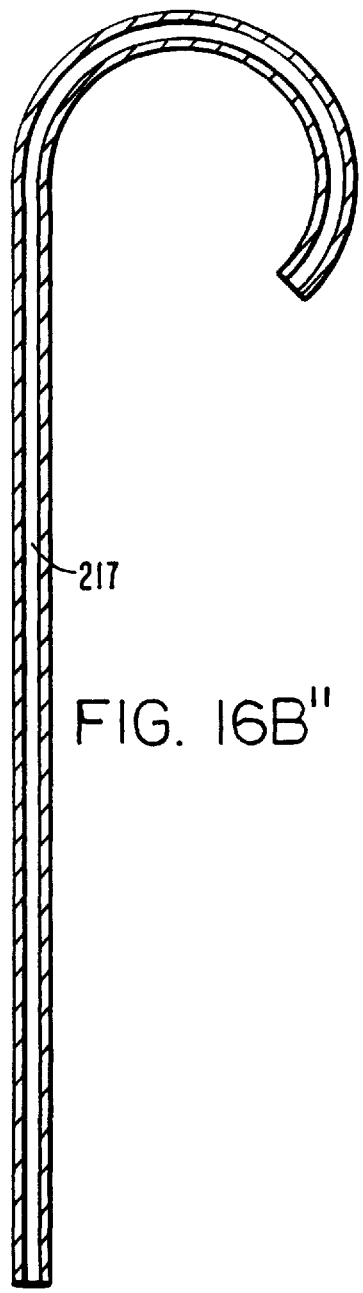
FIG. 16B'
FIG. 16B''
FIG. 16B'''

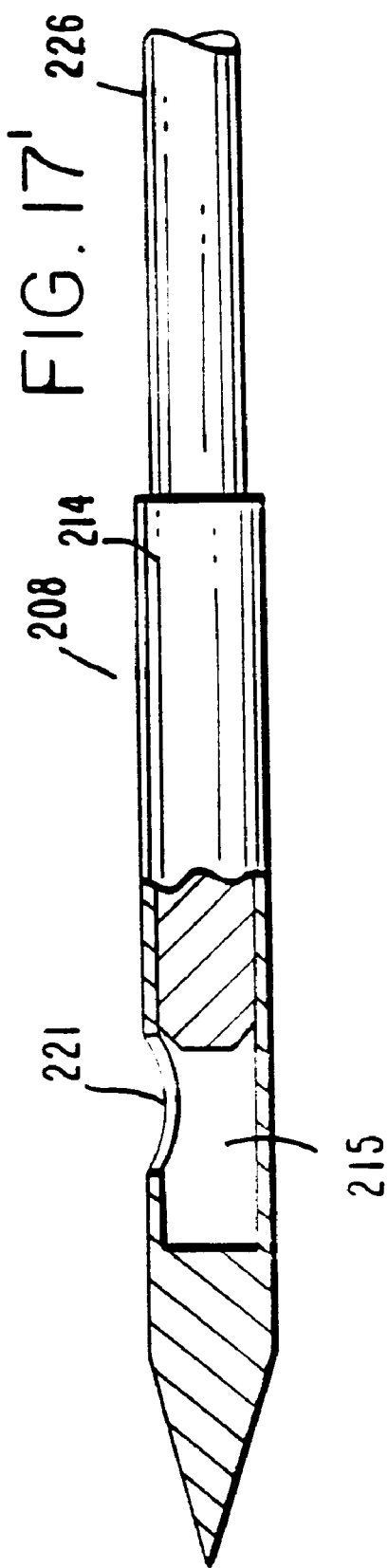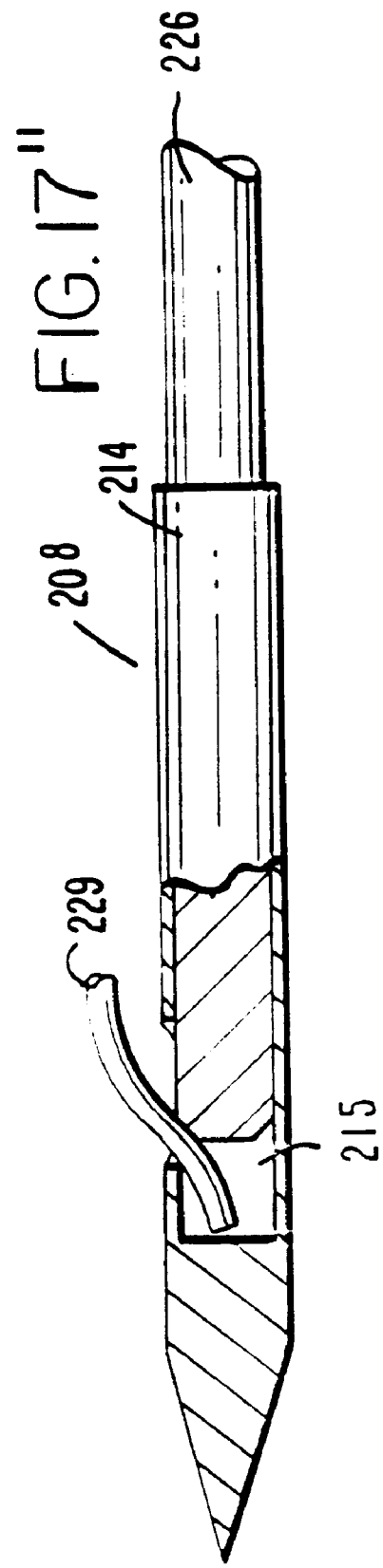

METHODS AND DEVICES FOR THE TREATMENT OF AIRWAY OBSTRUCTION, SLEEP APNEA AND SNORING

FIELD OF THE INVENTION

The present invention relates to surgical methods and devices, and more specifically, to methods and devices for the treatment of upper airway obstruction, obstructive sleep apnea and/or snoring.

BACKGROUND OF THE INVENTION

Obstructive sleep apnea (OSA) is a potentially life-threatening disorder, which affects up to 2–4% of the adult population. OSA, it has been determined, is associated with snoring, which affects 20% of adults. Both of these conditions can be triggered when the base of the tongue collapses during sleep, so that it partly obstructs the airway.

Various methods are known in the art for treatment of snoring and OSA, with varying degrees of success. Generally, the most successful non-surgical approach is continuous positive airway pressure (CPAP), in which a positive pressure is maintained in the airway to prevent blockage. CPAP, however, requires that the patient sleep with a respirator mask over his or her face, with a bedside air compressor to supply positive air pressure to the mask. Because of the discomfort and inconvenience, patient compliance with CPAP therapy is low, and 60% of patients who commence using CPAP stop using the apparatus within three months.

Oral appliances, such as "SnorBan," distributed by SnorBan of Rancho Cordova, Calif., generally operate by holding the patient's jaw forward. These appliances generally require careful fitting, and relatively few patients find them comfortable enough to sleep with them in place through the entire night.

Surgical procedures for treatment of snoring and OSA include uvulo-pharyngeal-palatoplasty (UPPP), midline glossectomy, hyoid suspension and tracheotomy. In UPPP, the lateral portion of the soft palate is removed, a painful procedure with high post-operative morbidity and only partial success. In midline glossectomy, a central, posterior portion of the tongue is removed, which is likewise associated with high morbidity, and requires a perioperative tracheotomy. Hyoid suspension, in which the tongue is pushed forwardly by tying the hyoid bone to the anterior mandible, is somewhat less invasive than the other procedures described, but has in the past been an open surgical procedure that has so far met with limited success. In serious cases of OSA, tracheotomy may be the only currently effective surgical treatment.

European patent application EP 0 743 076 A1, the teachings of which are incorporated herein by reference, describes an apparatus for treatment of sleep apnea by electrical stimulation of a patient's hypoglossal nerve. An electrode is positioned in electrical contact with a portion of the nerve, and a stimulating electrical current is applied to the electrode. The electrical current thus stimulates muscles of the upper airway, so as to cause contralateral extension of the patient's tongue and/or to increase the volume of the oropharynx. The apparatus requires, however, that the electrode be maintained in wired connection with an electronic nerve stimulator unit located outside the body. It also requires accurate and consistent contact with the nerve so as to avoid unwanted tongue movements.

SUMMARY OF THE INVENTION

It is an object of some aspects of the present invention to provide a less invasive surgical treatment for airway obstruction, OSA and snoring.

It is a further object of some aspects of the present invention to provide devices and methods to permit more effective anterior suspension of the base of the tongue, thus preventing collapse of the tongue into the airway during sleep.

It is a further object of some aspects of the present invention, to combine mechanical suspension of the tongue with other techniques for alleviating airway obstruction.

It is a further object of the present invention to provide devices and methods for anchoring the tongue to the mandible bone.

It is a further object of some aspects of the present invention to provide a set of improved screws for anchoring sutures to the mandible, hyoid or other bone.

It is a further object of the invention to provide improved anchors for fixation in the bones of the mouth.

It is a further object of the invention to provide improved bone anchor insertion devices.

It is a further object of the invention to provide improved suture passers.

In accordance with the preferred embodiments of the present invention, a method is provided for the treatment of airway obstruction by the fixation of soft tissue to bone. Specifically, the tongue is fixated to the mandible bone using bone anchors such as surgical screws. After attachment of one or more sutures to at least one bone anchor, the anchor is inserted into the mandible bone. The suture or sutures are then used to pull the tongue forward to clear the patient's airway. The sutures can be attached to one bone anchor or to two bone anchors, as desired. It is highly preferable that the suture(s) be under the skin at all points, although it is not necessary to achieve successful results.

A large number of variations are possible on the general method, as further described below. For example, the method can be conducted using one or two bone anchors, as desired. The anchors can be inserted directly into the mandible, or can be inserted into the mandible through the tongue. They can be inserted at the midline or in the sides of the mandible. Other variations are possible, too.

The procedures described can also be used to suspend the hyoid bone, with or without suspension of the tongue, to achieve the desired effect. Alternatively, the suspension of the hyoid bone can be accomplished by cutting an incision in the neck of the patient, inserting bone anchors having suture through the incision into the mandible and the hyoid bone, and fastening the suture(s) to achieve the necessary suspension.

Electrical neuro-muscular stimulation can also be employed in combination with any of the procedures disclosed herein to further improve the results obtained, if desired.

With respect to the bone anchors themselves, the bone anchor which is utlized is preferably a self-tapping (and possibly self-drilling) bone screw having a head which is crimped onto the suture. A hole, preferably axial, is provided in the head of the screw for securing the suture. The head of the screw is crimped to both secure the suture and provide a non-circular shape to the rear end of the anchor. This non-circular head can be driven by a correspondingly shaped socket of a power driver. Typically, one or two separate sutures providing 1, 2, 3, 4 or more strands or loops of suture, may be crimped to the screw.

The head of the screw is then driven by an anchor inserter with a socket to hold the anchor. The socket has a portion which can penetrate the bone, and which has an outer diameter preferably slightly less than the outer diameter of the threads of the screw. This permits the entire screw to be driven below the surface of the bone upon turning the socket. A second portion of the socket is provided but due to its larger diameter, can not penetrate the bone. The presence of a section having a diameter substantially larger than the diameter of the screw threads ensures this. Using the socket as a driving mechanism, the screw is mechanically rotated for insertion into the bone, with insertion continuing until the screw is completely beneath the bone's surface. The screw is turned until it self-exits from the end of the socket, to be securely fixed beneath the bone. The forward threading of the screw anchor to move out of the inserter. Then, when the screw anchor is disengaged from the inserter, the inserter senses the decreased torque and signals the operator. The anchor inserter can be either a linear or a nonlinear inserter, depending on which is more suitable for the particular suspension procedures.

In addition to the bone anchors and anchor inserters described herein, further description of bone anchors and anchor inserters are provided in U.S. Pat. No. 5,520,700 (filed Nov. 10, 1993), and U.S. patent application Ser. Nos. 08/572,682 (filed Dec. 14, 1995) and 08/804,172 (filed Feb. 21, 1997), the disclosures of which are incorporated herein by reference.

As also described herein, improved suture passers have been provided which are adapted for the procedures disclosed. These suture passers reduce the difficulty associated with threading the sutures through the mouth and the tongue in the necessary order and manner to effectively conduct the procedures.

Further aspects and features of the invention will become apparent in conjunction with the drawings and detailed description provided hereafter.

BRIEF DESCRIPTION OF THE DRAWINGS

FIG. 2A shows the bone screw of FIG. 1A, in a rear axial view, inserted into and between the jaws of a mechanical crimper with a line of suture extending out of the axial hole thereof.

FIG. 2B shows the bone screw of FIG. 1A and the crimper of FIG. 2A after the jaws have been closed so as to render a change of outside shape to the rear portion of the bone screw and to crimp the axial hole about the suture.

FIG. 13 is an exploded, perspective view of a bone contact indicator which attaches to the anchor inserter or screwdriver for providing an audible and/or tactile indication that the socket of the inserter has come into contact with the bone.

FIG. 14 is a plan view of an improved suture passer. The suture passer is provided with a primary needle and a secondary needle for simultaneous insertion of suture into two separate holes in the tongue. The suture passer is shown with the needles in the closed configuration.

FIGS. 16A and 16B are plan views of an additional improved suture passer (assembled in FIG. 16A and disassembled in FIG. 16B), in accordance with the present invention.

FIG. 17 is a plan view of a further suture passer, in accordance with the present invention.

DETAILED DESCRIPTION OF THE INVENTION AND THE PREFERRED EMBODIMENTS

In accordance with the method of the present invention, the treatment of airway obstruction is accomplished by the fixation of soft tissue to bone. In brief summary, and as described in greater length hereafter, the tongue of a patient is pulled forwardly and fixated to the mandible bone using bone/screw anchors such as surgical screws with attached suture. One or more sutures are attached to one or more bone anchors or bone screws. The bone anchors are inserted into the patient's mandible bone. The sutures are then passed through the tongue to complete a loop running from the base of the tongue to the anchor. By maintaining the loop under tension, the tongue is pulled forwardly to clear the patient's airway. As a result, surgical suspension of the tongue can be performed in a minimally invasive manner, without open incisions, unlike the surgical methods known in the prior art. In accordance with the present invention, airway obstruction, OSA and snoring can be relieved with reduced morbidity and less patient discomfort relative to other methods previously employed.

Figure 5:
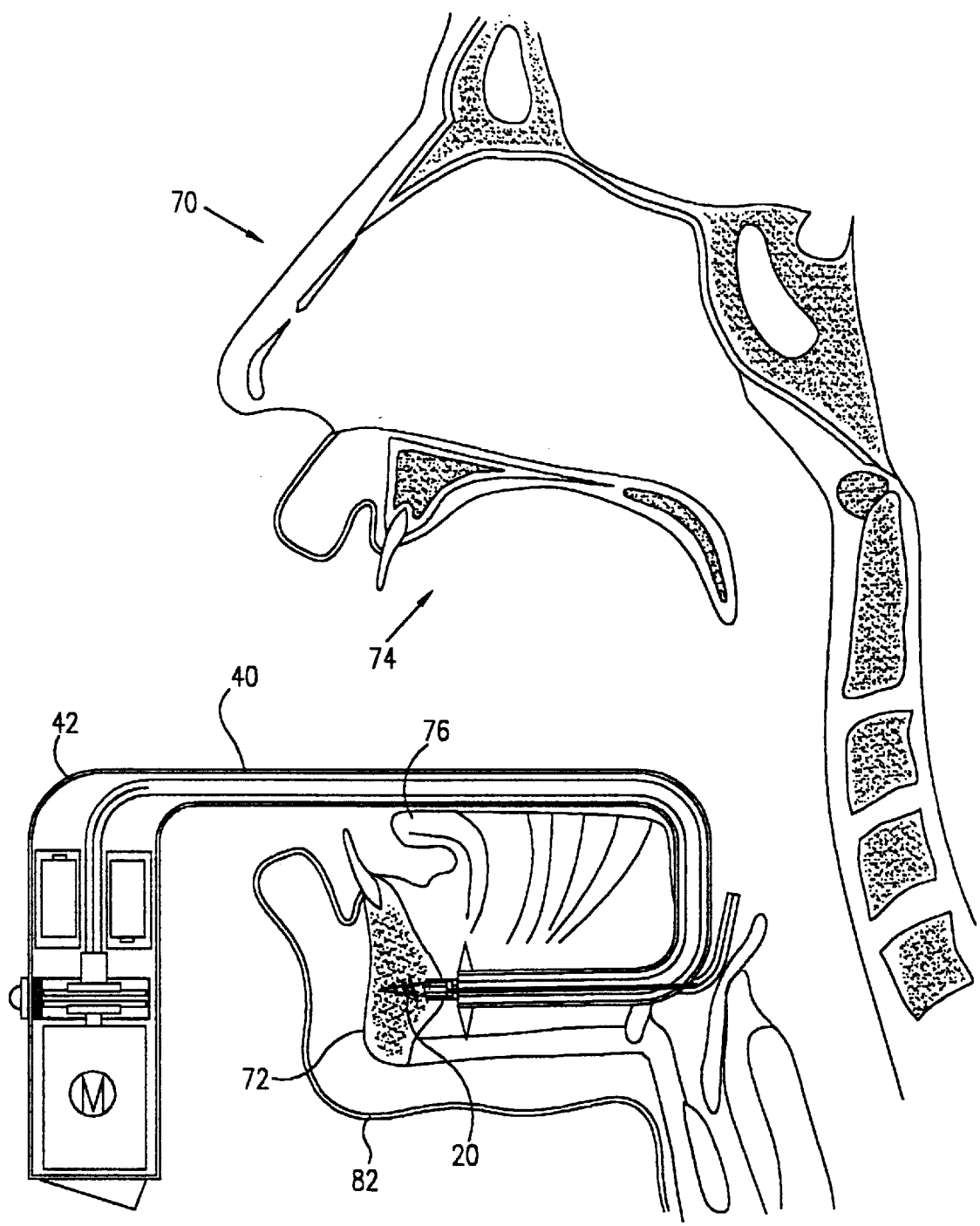
FIG. 5 is a partial, cross sectional view showing the positioning of the non-linear bone screwdriver of FIG. 4A, with the bone screw of FIG. 3, while the bone screw is being driven/inserted into the mandible of a human patient.

The procedure will be further understood with reference to the Figures herein. FIG. 5 illustrates a sagittal cross-sectional view through the head 70 of a human subject or patient. As shown in the Figure, a bone anchor or screw 20 having suture 32 attached thereto, is inserted into the subject's mandible 72 for use in an anterior tongue suspension. By use of the term "bone anchor", any form of anchor suitable for insertion and fixation in a bone is intended, whether a staple, a screw, or so forth. In the discussion which follows, the term bone screw is often used, in accordance with the preferred embodiment, although it is to be understood that other types of bone anchors may be employed without departing from the present invention.

To insert the bone screw 20 into the mandible 72, a screwdriver device 40 is placed into the subject's mouth 74, preferably while the patient is under general anesthesia. Bone screw 20 is held in socket 54 (see FIGS. 4A and 4B) at the screwdriver's distal end, as described more fully below. The screwdriver 40 is manipulated within mouth 74 so as to bring the distal tip of bone screw 20 to bear against the soft tissue at the base of tongue 76. The handle 42 of the screwdriver 40 is then pulled away from the patient's head 70 so as to force screw 20 through the base of tongue 76, until it reaches mandible 72. Preferably, screw 20 penetrates tongue 76 adjacent to the tongue's midline in both side to side and front to back directions, so as to avoid damage to nerves and blood vessels in the tongue and surrounding areas of the mouth.

Once the tip of screw 20 has made contact with the hard bone of mandible 72, screwdriver 40 is activated to drive the screw into the bone. Before activating the screwdriver, anatomical landmarks are used (for example, the positions of the incisor teeth and the lower edge of the mandible), to precisely position screw 20 against mandible 72 in such manner as to avoid contact with teeth and nerves during bone screw/anchor insertion. Thus, the screw 20 should be inserted into the mandible in an area near the mandible's midline, but below the area where the teeth may be affected. Axial force is applied to the screw either by pulling handle 42 away from head 70, or by attaching and gradually opening a vise, as is known in the art, located between the handle 42 and chin 82 of the patient's head 70. The anchor is driven through the floor of the mouth until it is below the surface of the bone. After screw 20 has been fully inserted into mandible 72, screw is disengaged from the socket 54 and the screwdriver 40 is removed from mouth 74.

Figure 6:
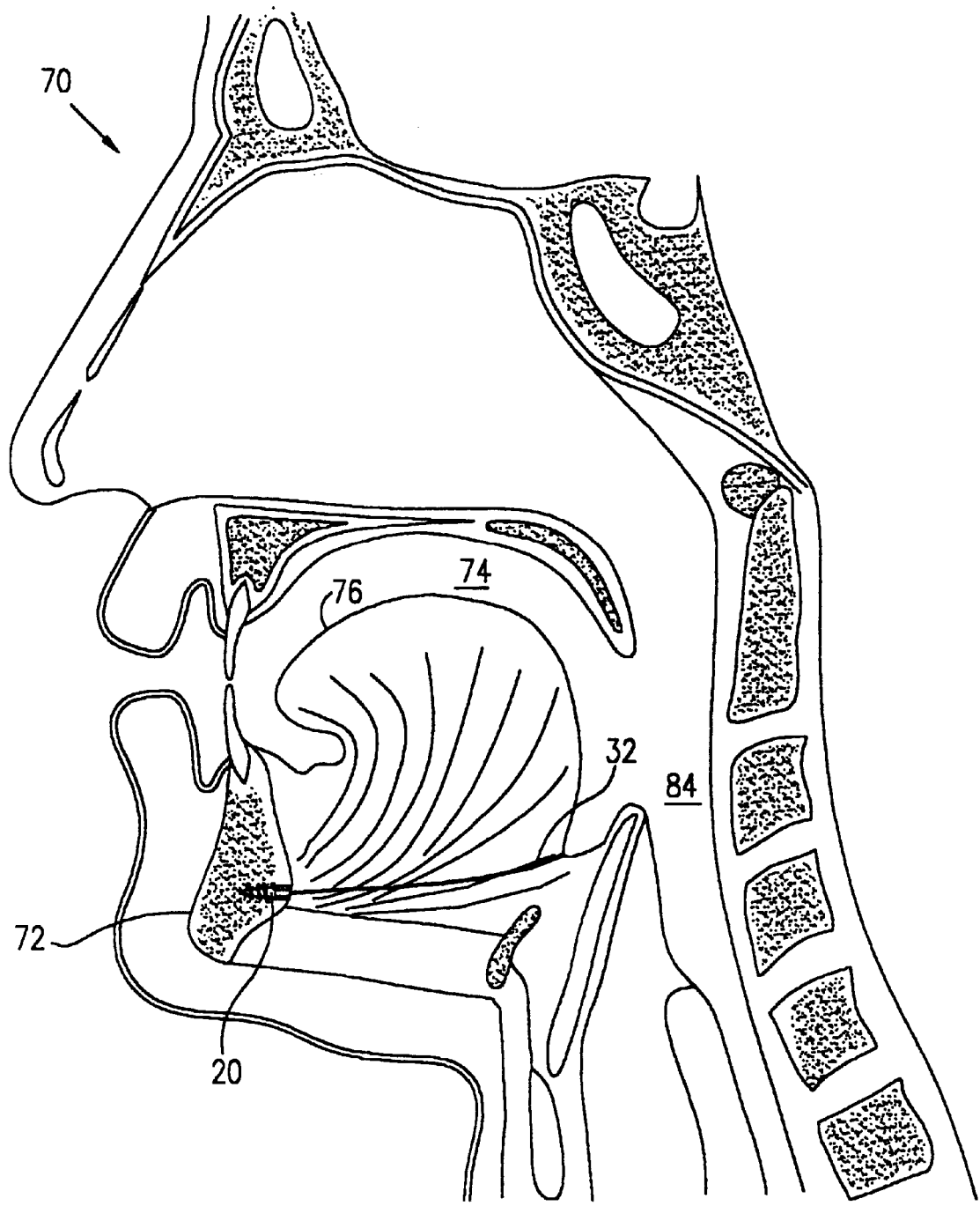
FIG. 6 is a partial, cross sectional view showing the location of the suture (which is secured to the bone screw in the mandible) to suspend the tongue of the patient.

FIG. 6 illustrates the next step in the tongue suspension procedure in accordance with one of the preferred embodiments of the invention. FIG. 6 is a cross-sectional view similar to FIG. 5, and uses two adjacent screws (one of which is not visible). After screwdriver 40 is removed from mouth 74, sutures 32, attached to screws 20, are drawn back behind the base of tongue 76. The ends of the sutures are then tied together with suitable tension to pull the tongue sufficiently forward toward mandible 72. This relative forward movement of the tongue relieves obstruction of airway 84. Preferably, the suture material is buried in the submucous layer at the tongue's base by passing with a needle. Healing and fibrosis of the area of sutures 32 will gradually cause adherence of the base of the tongue in the forward position. Due to the continual tension on the tongue, effected by the sutures, the patient's symptoms can be effectively alleviated.

The methods of the present invention can alternatively be accomplished using either one screw or using two screws. In other words, with a single screw, two sutures anchored to the screw can be tied together to achieve the necessary effect. With two screws, the screws may be positioned accordingly, with each having a suture thread or pair of threads extending therefrom. These sutures are then tied together to achieve the suspension and relative forward movement of the tongue.

A large number of other variations of this procedure are also possible. Although each of these address the problem in a slightly different fashion, in all of them the same objective is attained, i.e., permanently pulling the tongue forward to clear the patient's airway.

Figure 8A:
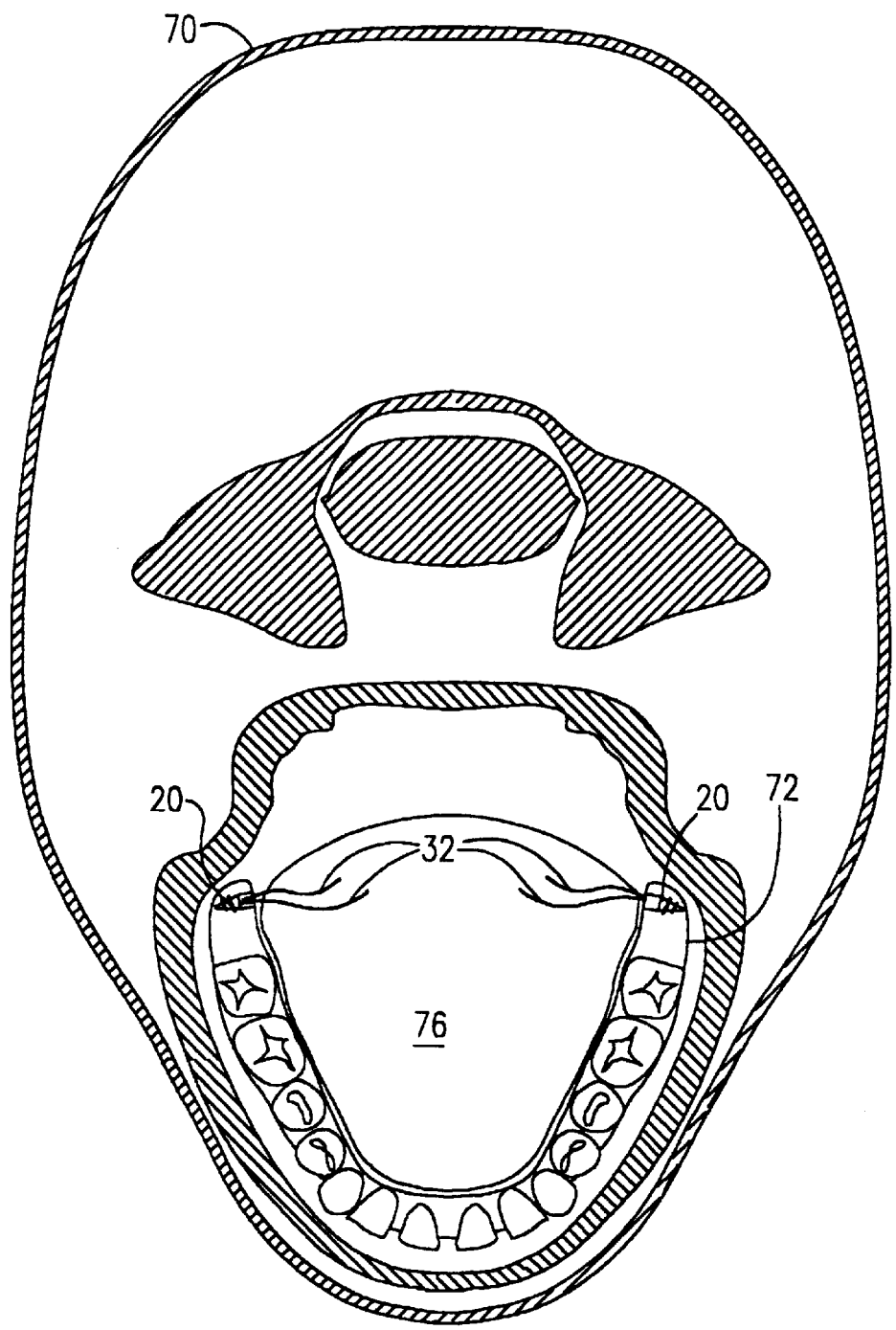
FIG. 8A is a top, cross-sectional view showing sutures secured to screws which are inserted into the sides of the mandible, with one screw on either side, in preparation for the suspension of the tongue of the patient by the sutures.

FIG. 8A, for example, is a cross-sectional illustration, in a downward axial view through the head 70 in a plane passing through the mouth, showing an alternative procedure for anterior suspension of tongue 76. In this case, screws 20 are inserted into the sides of mandible 72, rather than near the midline. A linear screwdriver, as is known in the art, may be used to insert these screws, rather than the nonlinear screwdriver 40. Each screw 20 is provided with a pair of sutures 32, as illustrated, for example, in FIG. 1B. Posterior molar teeth, which are normally found above the positions of screws 20, are omitted from the Figure for clarity of illustration.

The method of inserting screws 20 as shown in FIG. 8A is substantially similar to that described above. One or both of the pair of sutures 32 attached to each of screws 20 are passed through soft tissue at the base of the tongue adjacent to the screw, preferably by attaching a surgical needle to the suture, as is known in the art, and then passing the needle through the soft tissue. Each pair of sutures 32 are then tied together, preferably ipsilaterally, to suspend tongue 76 and to maintain it relatively forwardly and to thereby unblock the air passageway.

Figure 8B:
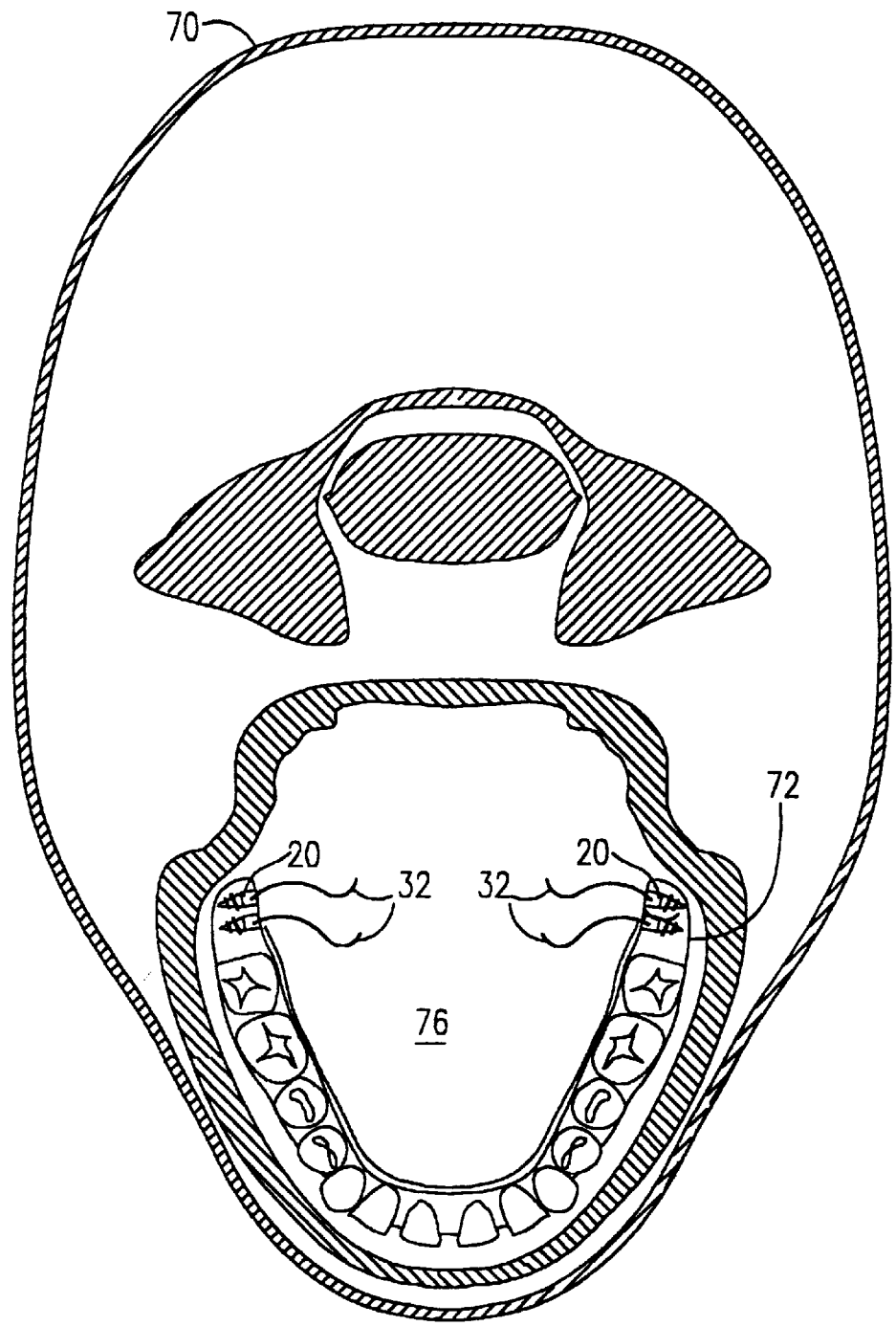
FIG. 8B is a top, cross-sectional view of a patient, similar to FIG. 8A, and showing sutures secured to a pair of screws inserted into both sides of the mandible, with two screws on each side, in accordance with an alternative embodiment of the present invention, in preparation for suspension of the tongue by the sutures.

FIG. 8B is a cross-sectional illustration in the same way as FIG. 8A, showing another variation of the procedure for suspension of tongue 76 from screws located in the sides of mandible 72. In this embodiment, two screws 20 are inserted side-by-side into each side of mandible 72, with four screws used in total. The suture 32 attached to one of the screws 20 on each side of mandible 72 is passed through the base of the tongue, just as described above with reference to FIG. 8A, and is then tied to a corresponding suture 32 attached to the other screw on the same side. Then the process is repeated on the other side. The two pairs of ipsilaterally-tied sutures provide stronger support to tongue 76 and may result in better long-term suspension of the tongue.

FIGS. 9A–9E are also cross-sectional illustrations, in a downward axial view through head 70 in a plane passing through the mouth, showing a further procedure and the sequential steps for anterior suspension of tongue 76. The procedure of FIGS. 9A–9E differs from that described in FIGS. 5–6 in that it is based on inserting a single screw 20 directly into mandible 72, rather than first forcing the screw through the base of tongue 76 and then driving the screw into the torque. This procedure may be easier for a surgeon to perform and less traumatic for the patient.

Figure 4A:
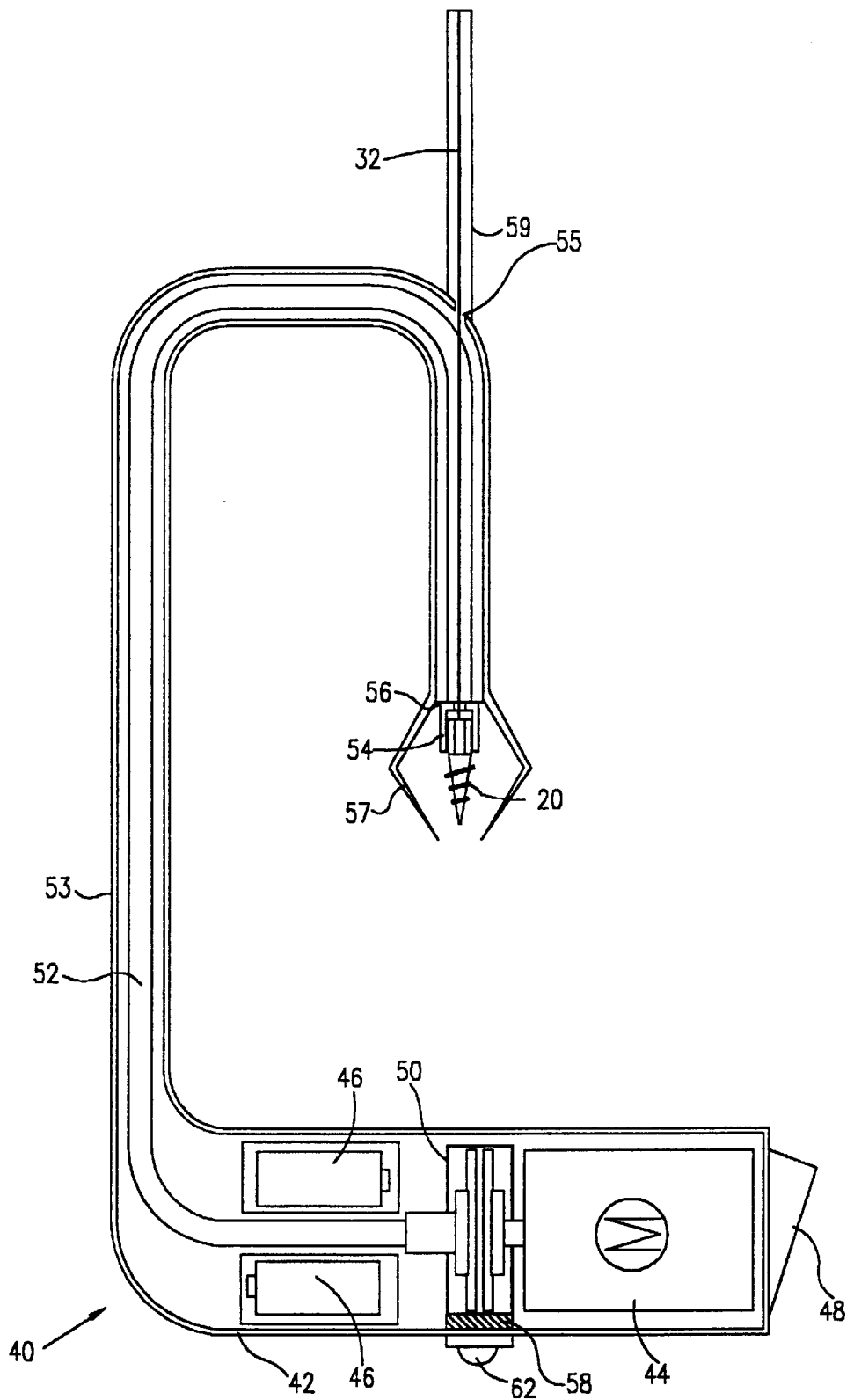
FIG. 4A is a partial sectional view, showing an electromechnical, nonlinear bone screwdriver device for driving the bone screw of FIG. 3 into bone.
Figure 4B:
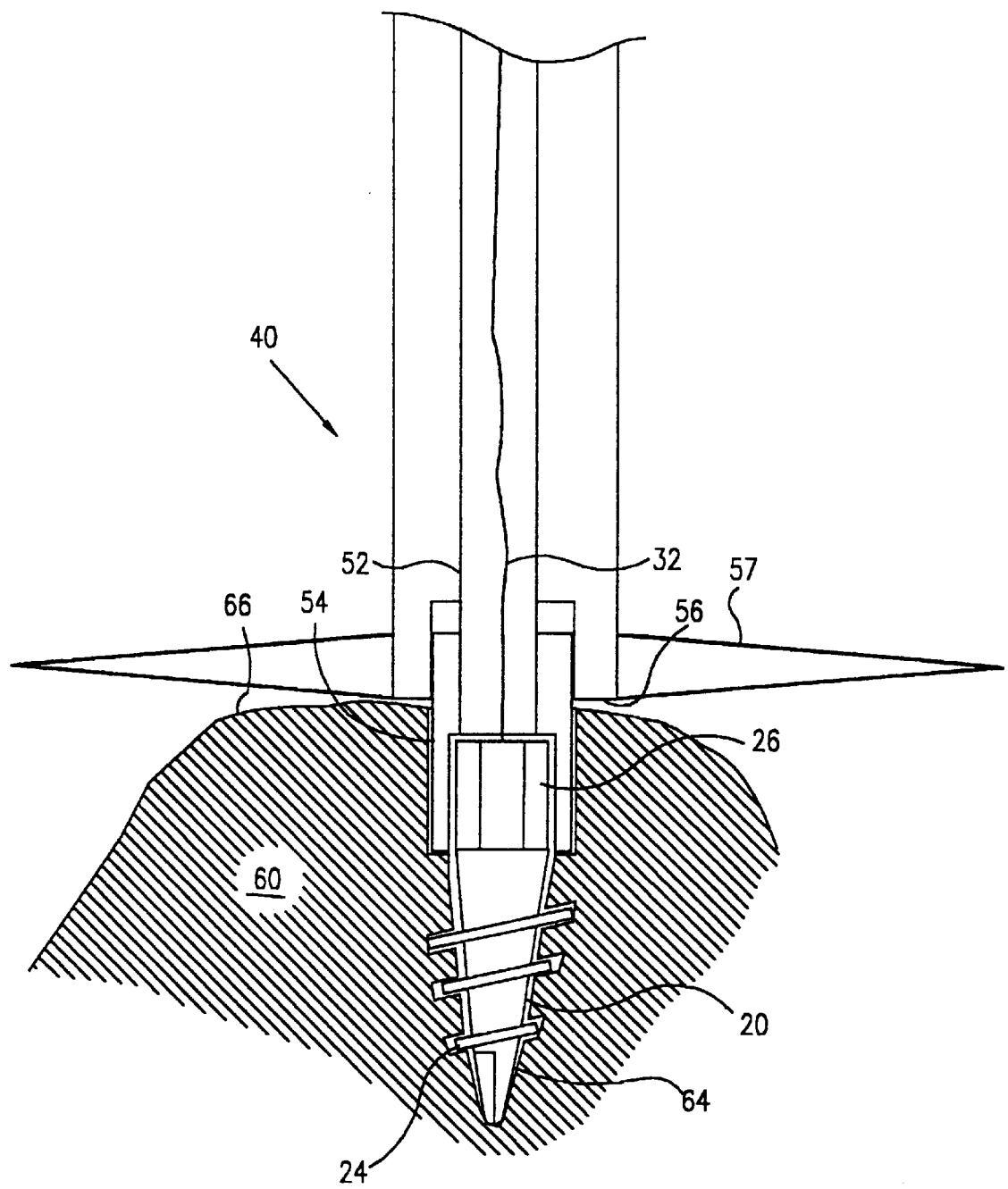
FIG. 4B is an enlarged, partial cross sectional view showing details of the screwdriver device of FIG. 4A and the bone screw of FIG. 3, during the process of driving the bone screw into the bone.
Figure 9A:
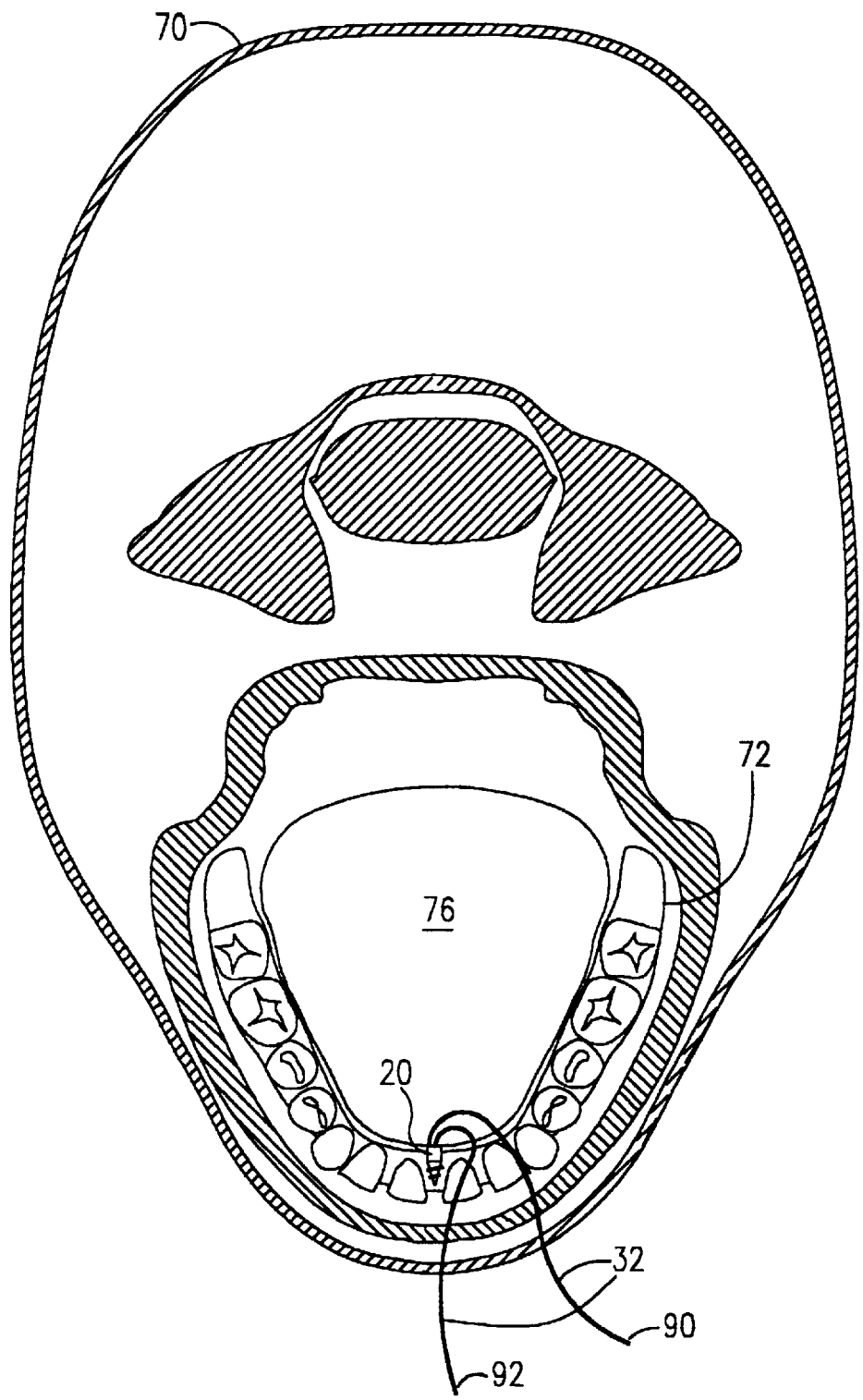
FIGS. 9A–9E are top, cross-sectional views illustrating and showing the sequential steps to be taken in a procedure for suspending the tongue by using a bone or screw anchor with attached suture. In accordance with this procedure, a bone anchor having suture attached thereto is inserted into the midline of the mandible, the suture will then be passed through the base of the tongue and tied in place.

As shown in FIG. 9A, the procedure begins with insertion of screw 20 into mandible 72, preferably at or adjacent to the midline of the mandible. The screw is preferably inserted using a nonlinear screwdriver, such as screwdriver 40, as shown in FIGS. 4A and 4B. It will be appreciated, however, that in the embodiment of FIG. 9A, the screwdriver may have a shorter shaft 53 (see FIG. 4A) than that shown for use in the other Figures. Preferably, suture 32 is passed through an eye or a loop fixed to the screw, as is known in the art, so that ends 90 and 92 (see FIG. 9A) may be easily adjusted, i.e., relatively lengthened and shortened.

Figure 9B:
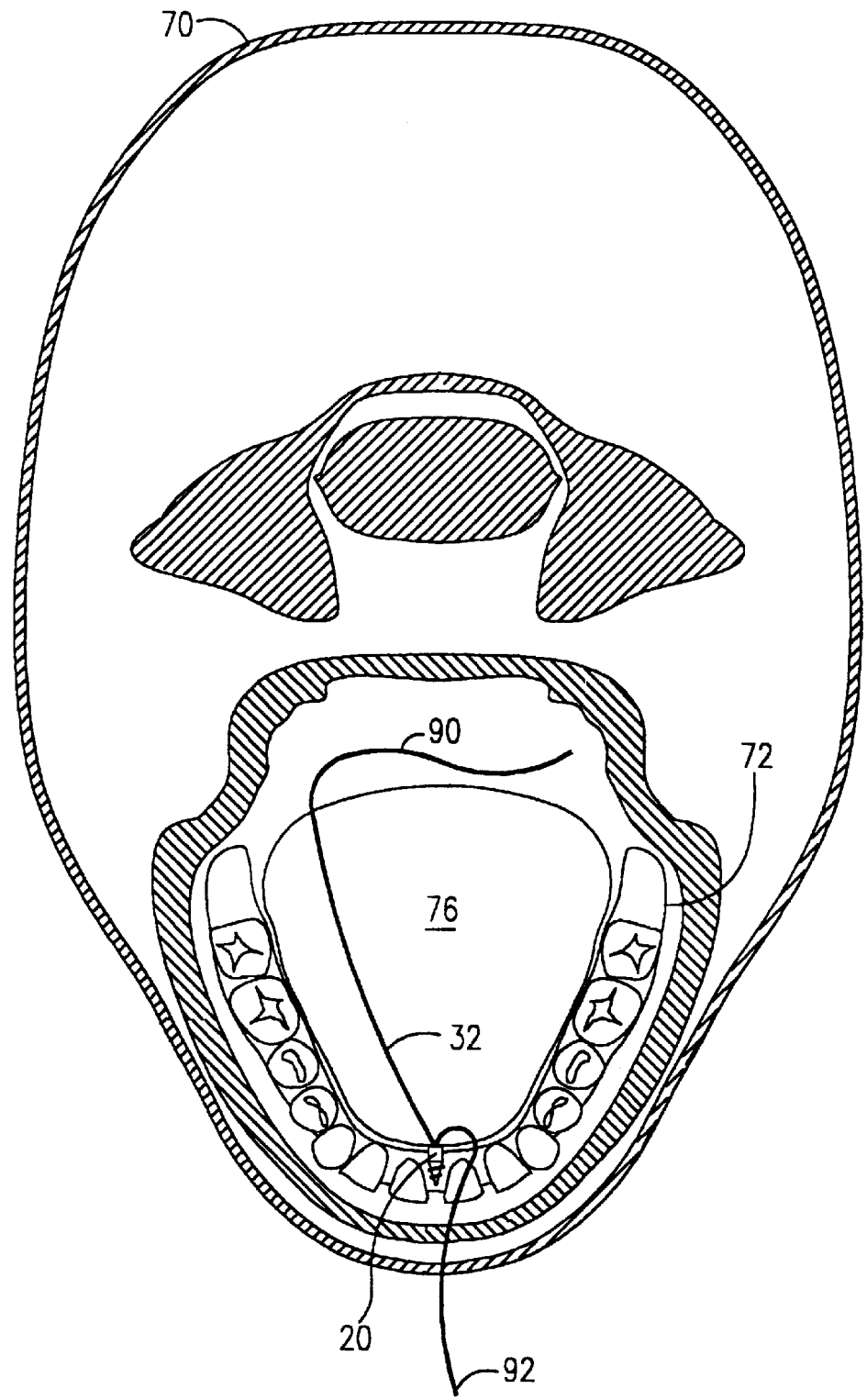
Figure 10:
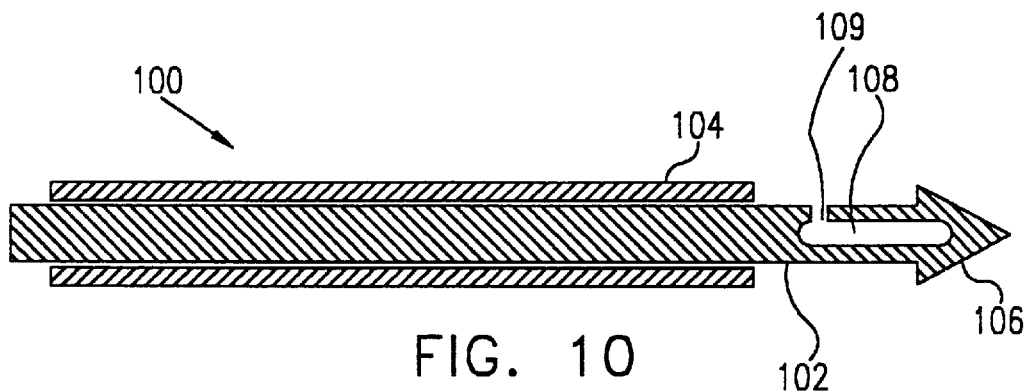
FIG. 10 is a cross-sectional view showing a suture passer which is useful for accomplishing the procedure illustrated in FIGS. 9A–9E.
Figure 11A:
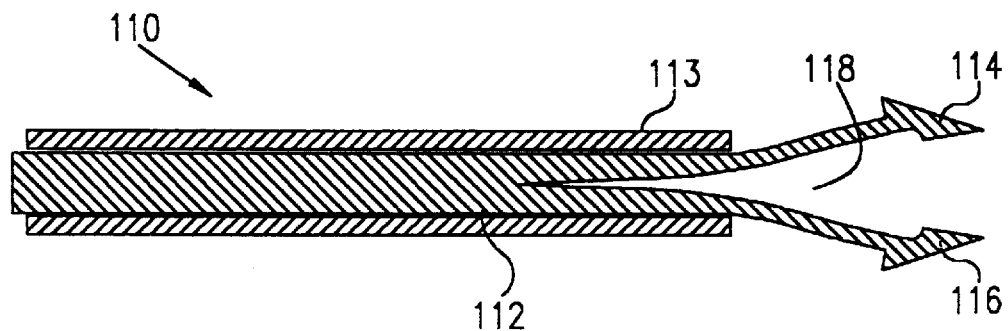
FIGS. 11A and 11B are cross-sectional views showing another embodiment of a suture passer useful in accomplishing the procedures of FIGS. 9A–9E. Both the open (11A) and the closed (11B) configurations, respectively, of the suture passer, are shown.

After inserting screw 20 in mandible 72, end 90 of suture 32 is passed posteriorly through one side of the base of the tongue, as shown in FIG. 9B. Preferably, a suture passer as shown in FIG. 10 or in FIGS. 11A and 1B is used for passing the suture through the tongue. Alternatively, any suitable surgical tool known in the art may be used for this purpose.

Figure 9C:
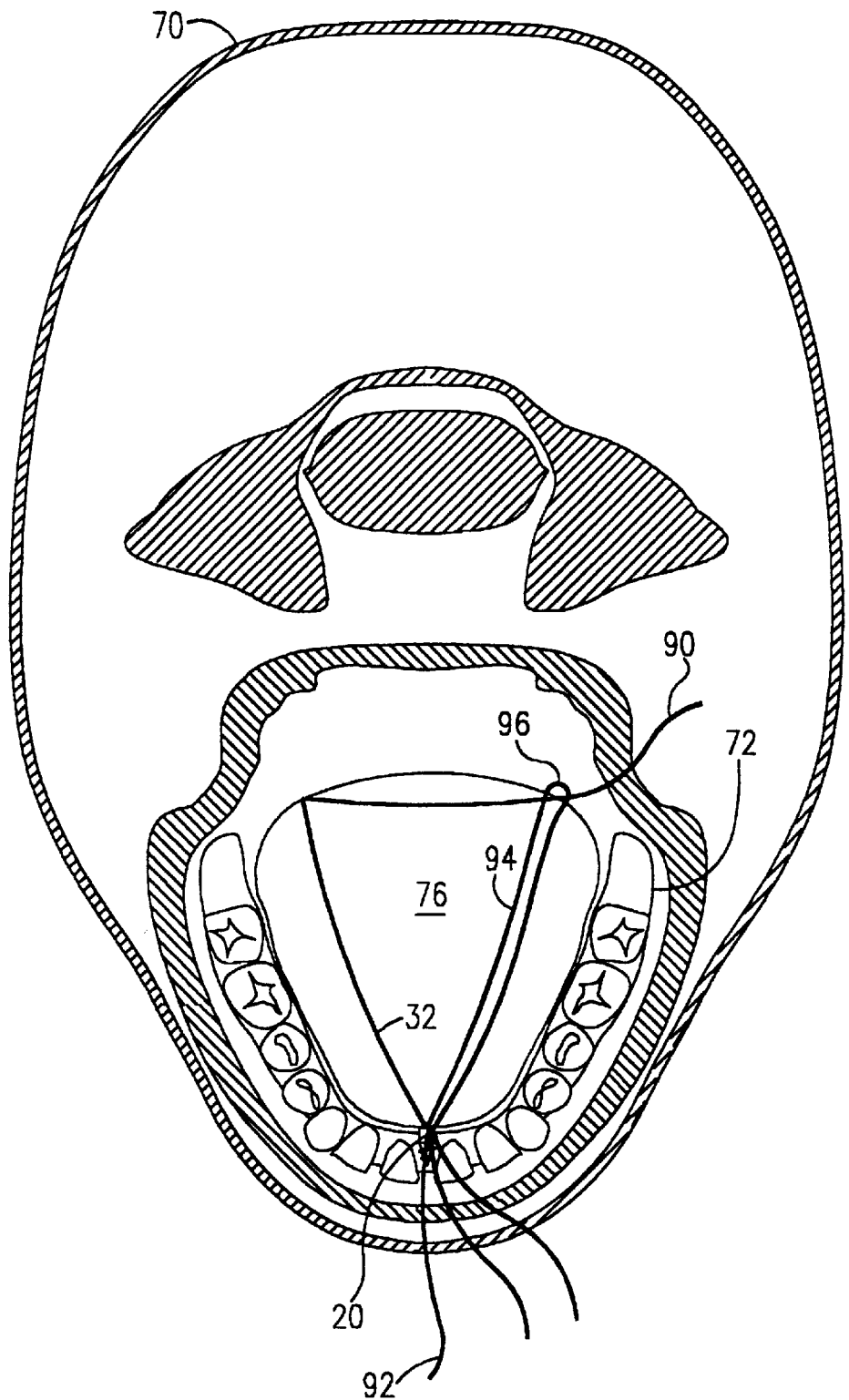

As shown in FIG. 9C, end 90 of suture 32 is next passed laterally, through the other posterior side of the base of tongue 76, preferably using a Deschamps needle, or any other suitable surgical tool known in the art. A second suture section 94 of suture 92, is folded to form a loop 96. It is also passed through the base of tongue 76 from front to back, so as to meet the end 90 of suture 32. End 90 is passed through loop 96. Alternatively, suture 94 may first be passed through the base of the tongue, and then end 90 of suture 32 may be passed laterally through the base of the tongue and through loop 96.

Figure 9D:
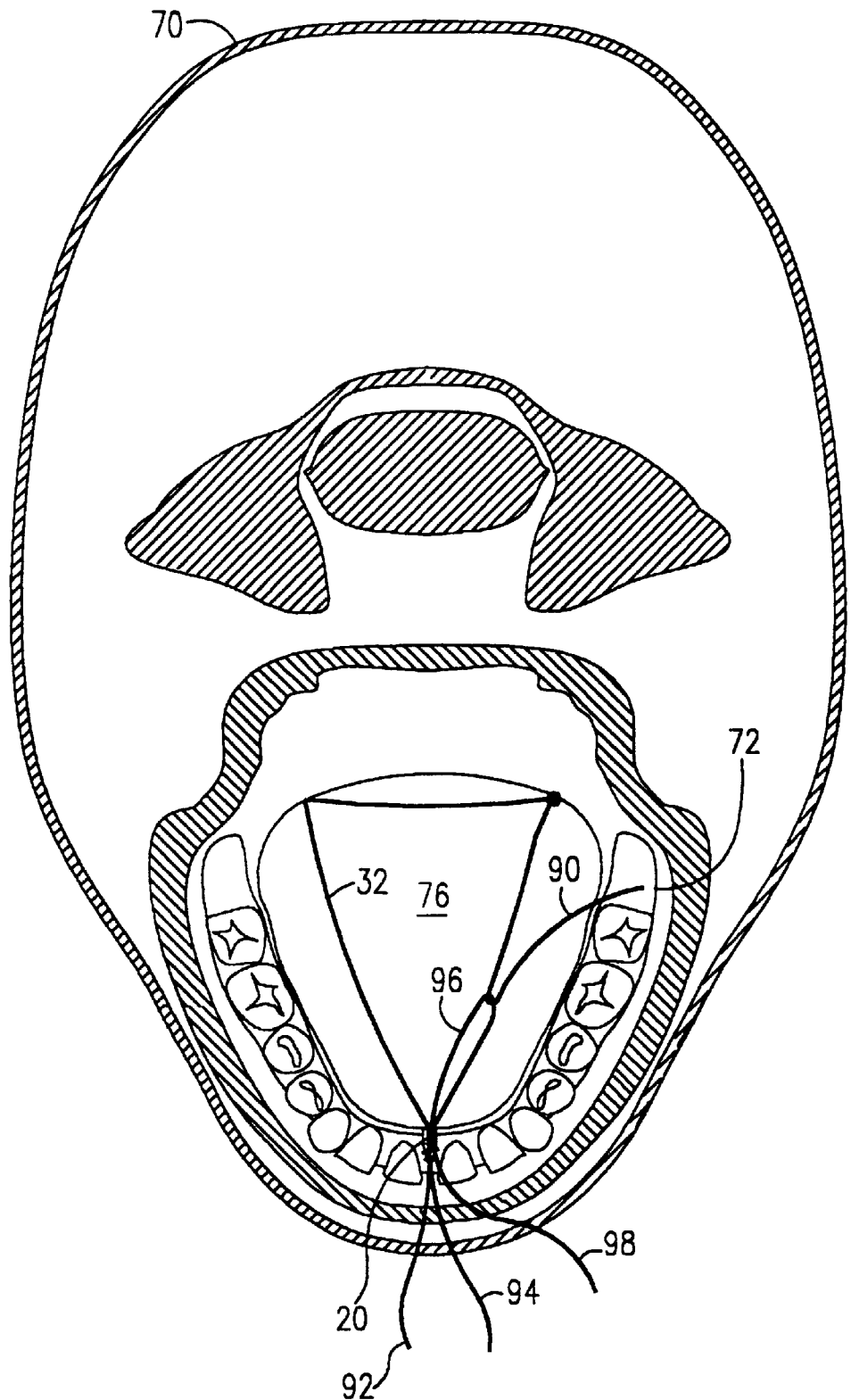
Figure 9E:
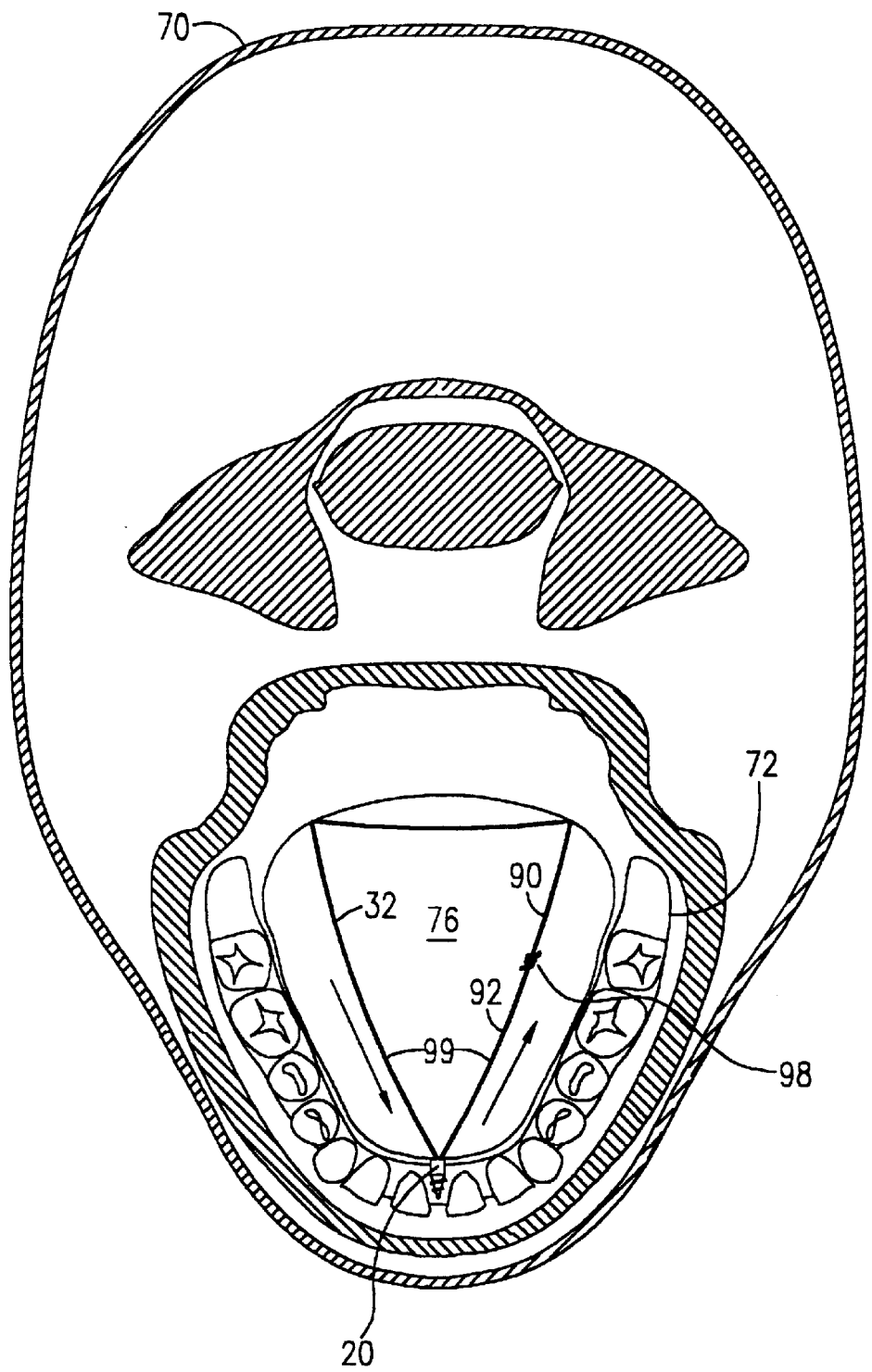

Suture section 94 is next drawn anteriorly out of tongue 76, thus pulling end 90 of suture 32 forward through the tongue, until suture 32 emerges in proximity to screw 20, as shown in FIG. 9D. Ends 90 and 92 of suture 32 are tied together in a knot 98, shown in FIG. 9E, with a tension sufficient to provide a desired degree of suspension of the tongue. Preferably, suture 32 is then drawn through the tongue in the direction of arrows 99, so that knot 98 is pulled unobtrusively under the tongue, where it will not disturb the patient.

In the preferred embodiment of the present invention, a single bone anchor with two sutures is placed into the mandible in an area near the midline, as discussed above. In this embodiment, a long suture passer is used to pass a first suture from the bone anchor and through the base of the tongue. This first suture is then released, and the second suture is subsequently grasped by the physician. This second suture can either be a completely separate suture from the first suture, or can be the second end of the suture extending from the anchor. This second suture is passed through the tongue, as was done with the first suture, except that in this case, a loop of the suture is left exposed through the base of the tongue, with both its ends being exposed in the floor of the mouth. A short suture passer is then used to pass the end of the first suture through the first hole in the base of the tongue, across the base of the tongue, out the second hole in the base of the tongue, and then through the exposed loop of the second suture. Pulling out the second suture by its ends in the base of the mouth thus drags the end of the first suture along with it. The two sutures from the bone anchor can then be tensioned and tied together to suspend the tongue, and the knot tied under the skin.

In another variation of the previously described embodiment, instead of using a loop of suture to pull the first suture back through the tongue, an empty, long suture passer is pushed through the tongue. After the first suture is passed across the base of the tongue to the hole formed by the suture passer, the passer grasps the suture and pulls it back out of the tongue.

Another variation on the method can be utilized in which the anchor in the bone has a small loop of suture attached to it. In this embodiment, the two ends of a separate suture are fed through this loop are then used to support the tongue. This allows the suture in the tongue to slide freely, and in addition allows the knot to be pushed more deeply into the tongue. These modifications increase the comfort of the patient.

A further variation on the method uses an anchor inserter with a long barrel, and is preferably conducted with two bone anchors. Each bone anchor is driven through the base of the tongue, through the tongue, until the anchor enters the mandible. One of the sutures is then passed across the base of the tongue and the two sutures are then tied together to provide the necessary forward pulling tension on the tongue.

In a further embodiment, a loop of suture may be passed through the tongue without piercing the base of the tongue. In this embodiment, an anchor is placed in the floor of the mouth in the mandible, near the centerline. A specially adapted suture passer is then used to pass the suture through the tongue until it approaches the base of the tongue. The suture is then looped around and back until it exits the tongue near the floor of the mouth in the region where it first entered the tongue. The two sutures can then be tied together as described above.

In addition to the embodiments discussed above, further variations on this procedure can be performing using suspension of the tongue by support provided by suture secured to the hyoid bone. Suspension of the hyoid can also be performed together with, or independent of, the suspension of the tongue.

Figure 7A:
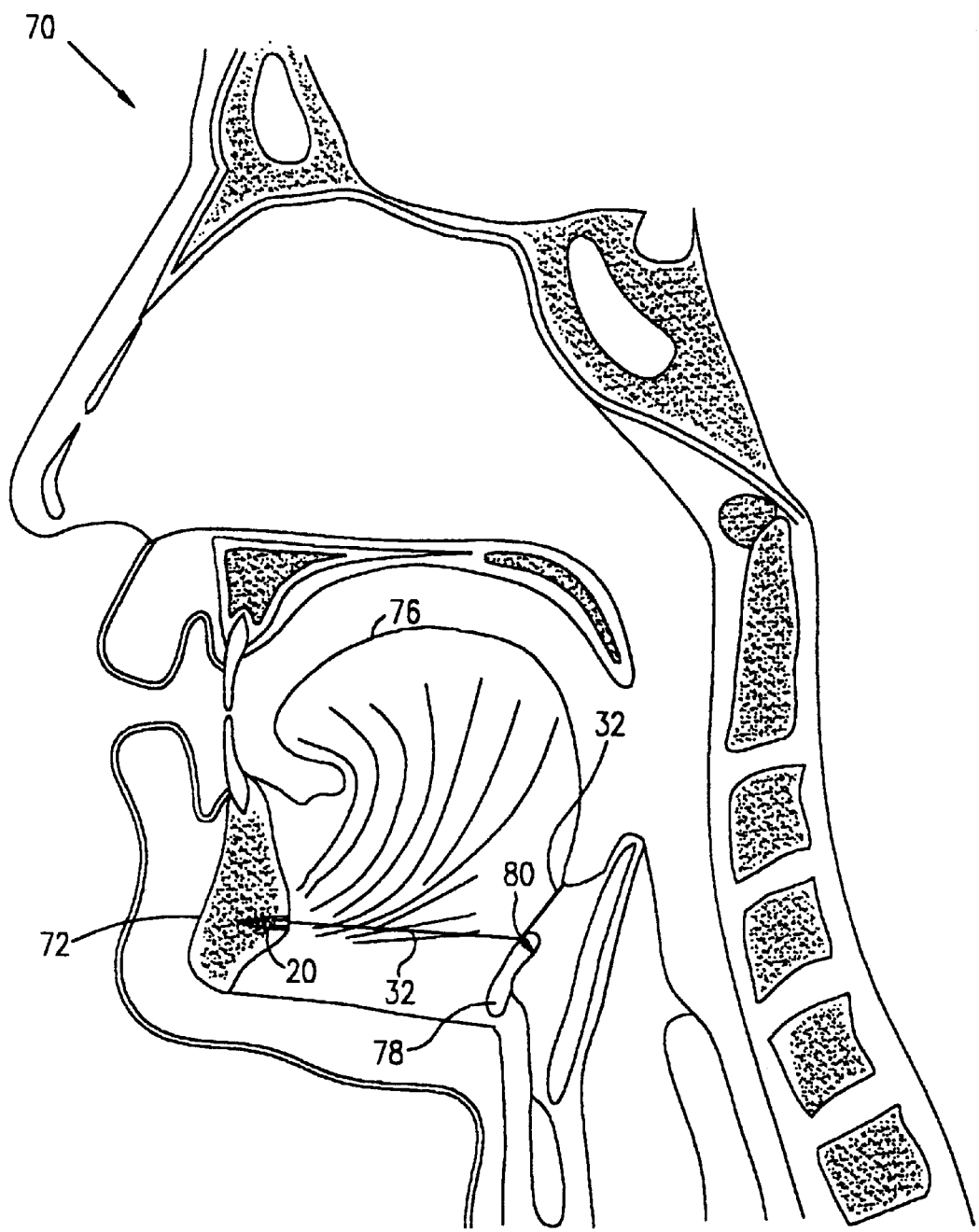
FIG. 7A is a partial, cross sectional view showing the location of suture, secured to a bone screw in the mandible and to the hyoid bone, to suspend the tongue of the patient.

For example, FIG. 7A is an illustration in sectional view of an alternative procedure for anterior suspension of tongue 76 using the patient's hyoid bone. In addition to insertion of screws 20 into mandible 72, as described above, an additional screw 80 is driven into hyoid bone 78. Preferably, screw 80 is substantially similar in construction to screw 20, but should be smaller in size due to the relative size of hyoid bone 78 in the human anatomy.

Screw 80 may have either one suture 32 attached thereto, or two such sutures, as discussed above. In either case, sutures 32 are tied together so as to pull hyoid bone 78 forwardly toward mandible 72, and to simultaneously suspend the base of tongue 76. In some cases, suspension of the hyoid bone together with the tongue may have greater long-term effectiveness in keeping airway 84 clear then suspension of the tongue provided by the screw in the mandible, alone.

Figure 7B:
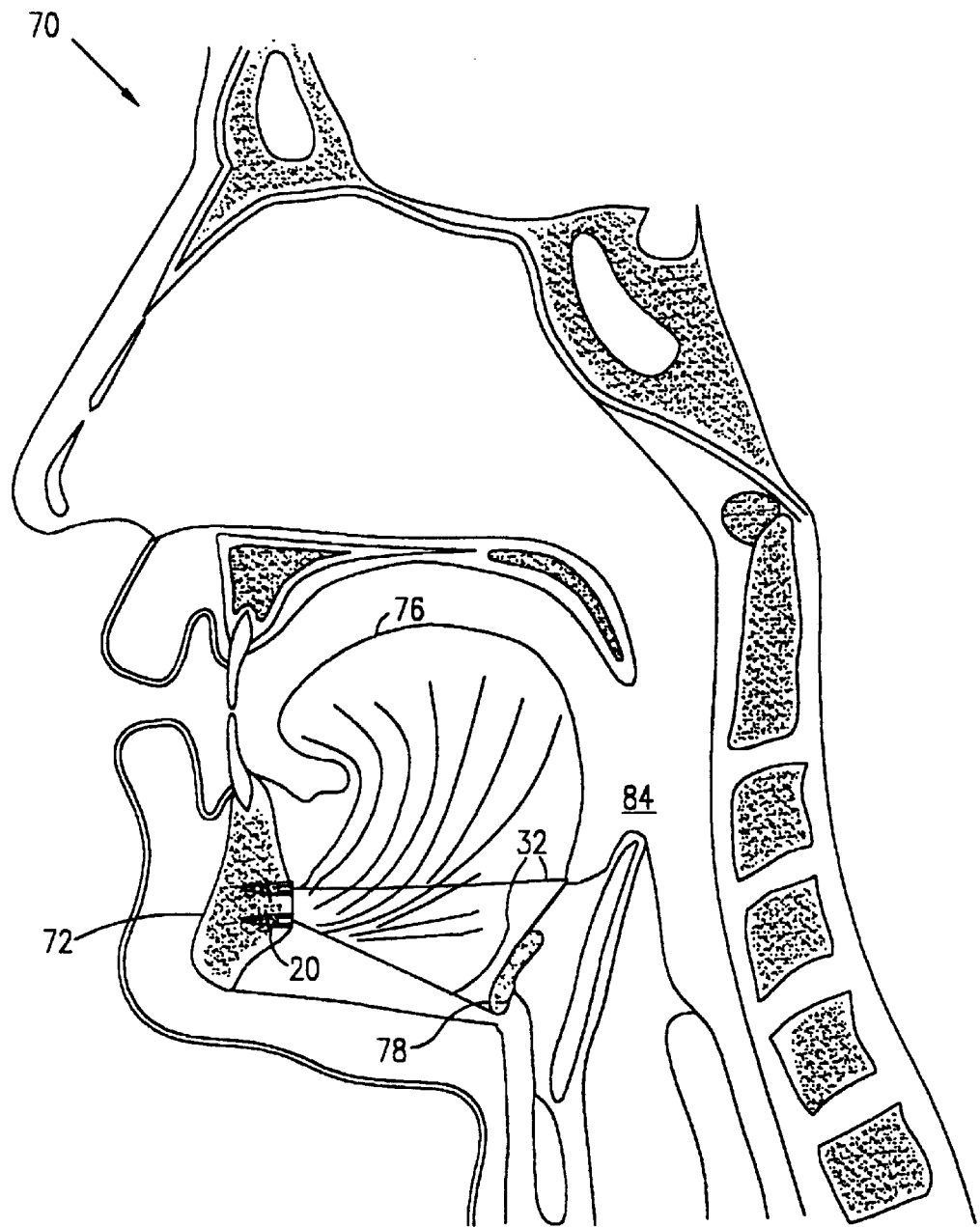
FIG. 7B is partial, cross sectional view showing suspension of the tongue and hyoid bone of a patient using sutures secured to two bone screws located in the mandible.

An alternative procedure for suspending tongue 76 and hyoid bone 78 is shown in FIG. 7B. In this procedure, instead of inserting screw 80 into hyoid bone 78, sutures 32, attached to screws 20 in mandible 72, inserted as described above, are passed intraorally around hyoid bone 78. Preferably, as shown in FIG. 7B, two screws 20 are inserted, one above the other, generally at the midline of mandible 72. The suture 32 attached to the lower screw of screws 20 passes below and behind hyoid bone 78, generally along a sagittal axis at the midline of the bone, while the suture 32 attached to the upper screw of the screws 20, passes above the hyoid bone on this axis. These sutures are preferably passed above and below the mylohyoid muscle, adjacent to hyoid bone 78, and are tied together to suspend the hyoid bone to the screws in the mandible.

Although in the preferred embodiments described above, anterior suspension of hyoid bone 78 is performed in conjunction with suspension of tongue 76, it will be understood that similar procedures may be used, in accordance with the principles of the present invention, to suspend hyoid bone 78 to mandible 72, with or without the insertion of a screw 80 in the hyoid bone. Such hyoid bone suspension may be performed intraorally, as described above, or alternatively through a small incision in the neck.

In conjunction with the various embodiments of the present invention, the methods of suspending the base of the tongue described above can also be combined with electrical nerve stimulation of muscles of the upper airway, as described in the European patent application EP 0 743 076 A1, the disclosure of which is incorporated by reference. In this method of electrical neuromuscular (nerve and muscle) stimulation, it is preferable that at least one electrode with an accompanying electrical lead or wire be fixed to one of the sutures passing through the base of the tongue. The wire connects the electrode to a power source within the patient's mouth. The power source is preferably implanted in or adjacent to the mandible. The electrode may comprise either a unipolar or a bipolar electrode, as both are known in the art. It may also consist of an array of electrodes distributed along the suture material.

Figure 12:
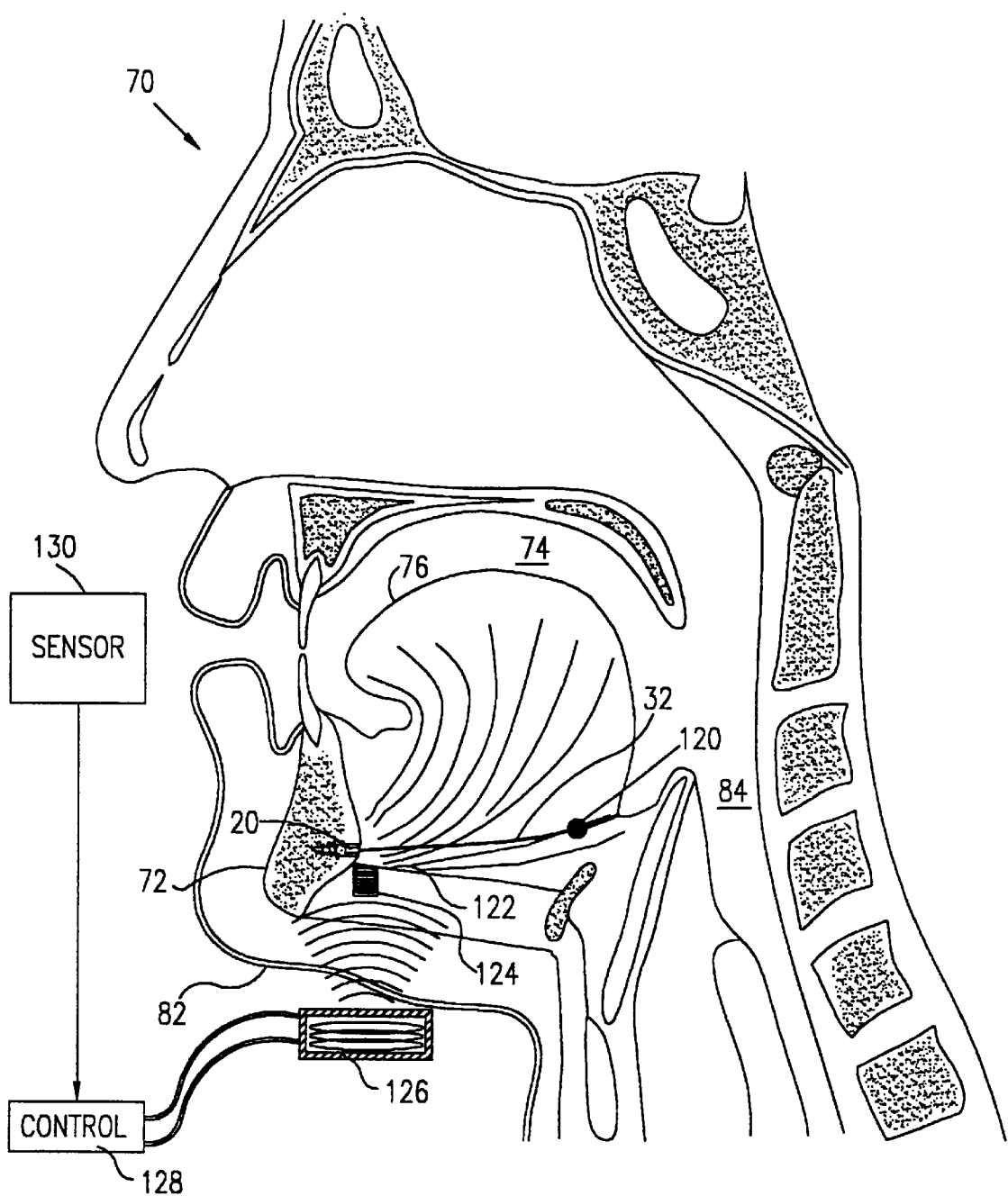
FIG. 12 is a side, cross-sectional view of a patient showing an electrode which is implanted in the mouth of a patient for electrically stimulating the muscles of the patient's upper airway. The Figure also shows a remote, external controlling unit.

One such embodiment is shown in FIG. 12. FIG. 12 depicts a sagittal sectional view through head 70, and illustrates the implantation and use of an apparatus for electrical stimulation of muscles associated with airway 84. The implantation is preferably performed in conjunction with an anterior suspension of tongue 76, as shown and described above, for example, with reference to FIG. 6 or FIGS. 9A–9E.

As shown in FIG. 12, a stimulation electrode 120 is fixed to suture 32 (secured by screw 20, in the mandible) and is thereby positioned at a suitable location at or within the base of tongue 76. Electrode 120 is electrically coupled to a miniature induction coil 124 by a wire 122, running along suture 32, either parallel to or contained within the suture. Coil 124 is preferably fixed to mandible 72 or, alternatively, is implanted in a suitable hole drilled in the mandible. Electrode 120 may comprise either a bipolar or a unipolar electrode, as both are known in the art.

In order to stimulate the airway muscles, a driving coil 126 is brought into external proximity with implanted coil 124. For example, this can be done by positioning the driving coil under chin 82 of the subject. Driving coil 126 is driven with a suitable electrical current by a controller 128, creating a magnetic field along an axis of the coil. The magnetic field generates a corresponding current in coil 124, which energizes electrode 120 to stimulate tongue 76, as well as other muscles of airway 84, as described in European patent application EP 0 743 076 A1. Such muscle stimulation cooperates with mechanical suspension of the tongue by screw 20 and suture 32 to provide greater relief of airway obstruction.

This method of electrical stimulation, using a miniature induction coil, is further advantageous, by comparison with stimulation methods known in the art, in that there is no need for a hard wired connection between electrode 120 and controller 128 or any other electrical drive unit located outside mouth 74. Electrical power is entirely received by the induction coil from the driving coil and the associated control circuitry outside the mouth (typically beneath the patient's chin). Thus, the patient is relieved of the discomfort and potential safety hazard of electric wires, with current flow, running through his or her mouth. Generally, the patient will put driving coil 126 in place beneath his or her chin 82 before going to sleep and will then activate control unit 128. There is thus no need for wires to pass between the patient's mouth and the control circuitry, in contrast to the European patent application referred to above.

Preferably, as shown in FIG. 12, control unit 128 further receives signals from a sensor 130, indicative of the subject's nocturnal breathing pattern, and activates coil 126 to drive electrode 120 accordingly, when the signals indicate a possible obstruction of airway 84. Sensor 130 preferably comprises a microphone, placed in any convenient location, for sensing/detecting snoring noises. Additionally or alternatively, sensor 130 may comprise an air flow sensor, placed adjacent to the subject's mouth, or a motion sensor, placed on the subject's chest. Further alternatively, a tension sensor, for example, a piezoelectric element or strain gauge, may be placed on or in proximity to the tongue 76, and provide feedback to control unit 128 regarding the tongue's muscle position as a function of its muscle tone. It will be understood, however, that control unit 128 can also operate without the use of sensor 130, according to a predetermined programmable stimulation pattern.

Although the electrode and power source are preferably permanently implanted in the patient's mouth, they are generally intended to be operated only at night. Thus, before going to sleep, the patient fixes the driving coil in place and turns on the control circuitry. The circuitry preferably activates the electrode responsive to feedback indicative of abnormal breathing, for example, by sensing snoring noise, chest motion, reduction of air flow through the mouth or muscle tension of the tongue. Alternatively, the circuitry may activate the electrode continually, according to a predetermined on/off pattern.

Thus, as described above, numerous methods are provided for treatment of airway obstruction in accordance with the present invention. These methods involve suspension of the tongue and/or hyoid bone, using bone anchors having suture attached thereto. The methods may further involve electrostimulation of the muscles of the tongue, as desired.

Further variations on any of the embodiments disclosed herein are also possible. For example, any of the prior embodiments can be combined with devices which measure tension in the suture when it is knotted. Similarly, any of the embodiments of the method can be combined with elastic members which are used with the suture and left in the tongue to limit or control the tension in the suture. The embodiments can also be combined with a sling which is added to the suture or which replaces the suture, as such a sling may be less likely to cut through the tongue over time. Likewise, any of the methods of the invention can be used in conjunction with clips which allow the suture to be shortened or lengthened during the surgery procedure or at a later date.

In addition to the above described methods, bone anchors and insertion procedures, in accordance with the principles of the present invention, may also be used to treat vocal cord paralysis, another result of airway obstruction. In this case, one or more screws are inserted into the thyroid cartilage. Sutures attached to the screws are then tied around the vocal cords, so as to lateralize one of the vocal cords and alleviate the airway obstruction.

To accomplish the procedures described herein, a variety of different tools and devices are provided, as described further below. These tools and devices are especially made and adapted for accomplishing the objectives of the disclosed methods. These tools and devices include bone screws or anchors, anchor inserters and suture passers.

Figure 1A:
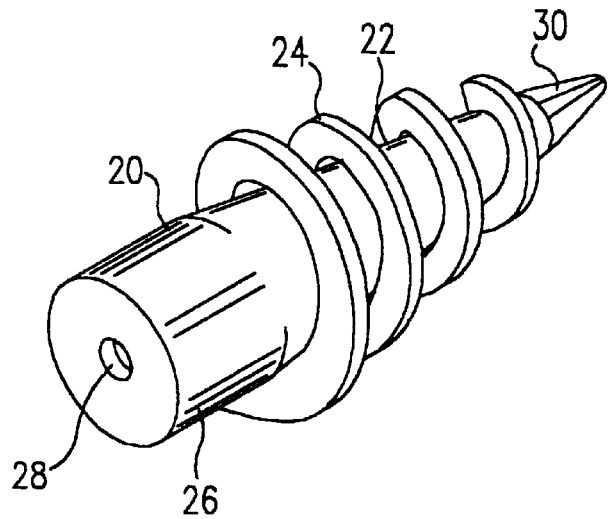
FIGS. 1A and 1B are rear perspective views of two preferred bone screw embodiments, in accordance with the present invention yet prior to crimping suture into the holes and before changing the rear end.
Figure 1B:
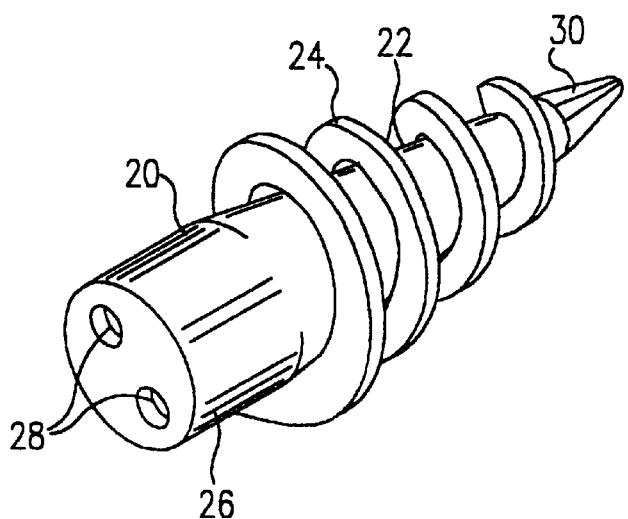

A preferred original form of a bone anchor 20 for use in the procedures/treatment disclosed above is illustrated in FIG. 1A. Bone anchor 20 is preferably a self-tapping bone screw, or in other words, is a bone anchor or screw which is capable of insertion into the bone without the need to predrill a hole in the bone. The threads of the anchor drill into the bone and secure the anchor in the bone.

It is further preferred that screw 20 include an axial notch 30 in the distal portion 22, so that the screw is self-drilling, as well. This self-drilling feature, as is known in the art, is particularly useful since the screw is being driven into the mandible, which is a relatively hard bone.

In a preferred embodiment, bone screw 20 includes a generally conical distal portion 22 having an external, spiral thread 24, and a generally cylindrical proximal portion 26. Thread 24 preferably has a substantially greater diameter than proximal portion 26, for reasons that will be described below. Proximal portion 26 includes an axial hole 28, which receives a suture.

Screw 20 is preferably made of biocompatible stainless steel, more preferably 316L stainless steel or titanium. Alternatively, the screw may be made of any suitable biocompatible material, including absorbable and biodegradable materials known in the art.

As shown in FIG. 1B, which schematically illustrates screw 20 in accordance with an alternative preferred embodiment of the present invention, proximal portion 26 may include two holes 28, for receiving two sutures. Or, proximal portion 26 may include a greater number of such holes, dependent on the number of sutures to be attached to the screw.

The suture itself is preferably secured to the screw using a crimping operation. FIGS. 2A and 2B illustrate a preferred embodiment of a crimping operation applied to screw 20, in preparation for insertion of the screw 20 into the bone or mandible of a subject, as described above. The screw 20, as seen in these Figures is shown in an axial view. As depicted in FIG. 2A, proximal portion 26 of the screw is held in a hexagonal notch 35 defined between jaws 34 and 36 of a crimper mechanism 38. Jaws 34 and 36 may comprise any suitable material hard enough to compress the proximal portion 26 of screw 20 into the desired form when the jaws are moved toward one another. The jaws are preferably driven by a vise or other means known in the art. A surgical suture 32 is first inserted into axial hole 28 of the screw 20. As depicted in FIG. 2B, jaws 34 and 36 are then closed or moved towards one another, so that hole 28 firmly closes around suture 32, and, at the same time, the proximal portion of the screw is pressed into a hexagonal shape. Although a hexagonal shape is shown and is the preferred embodiment, the proximal portion of the screw can be crimped to provide a nonpolygonal shape, as well.

Figure 3:
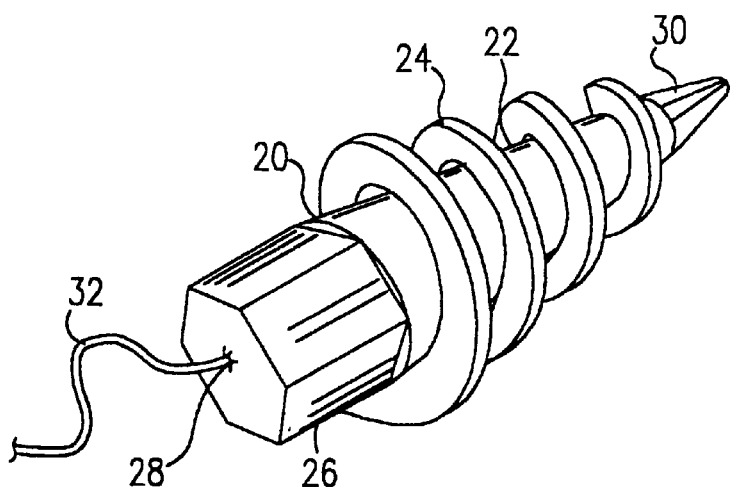
FIG. 3 is a rear perspective view of the bone screw shown in FIG. 1A, after crimping of the screw has been accomplished by the jaws of FIGS. 2A and 2B.

FIG. 3 illustrates screw 20, shown originally in FIG. 1A, after the crimping shown in FIG. 2B. The crimping operation applied to the screw has, in a single step, both fastened suture 32 to the screw and converted proximal portion 26 into a hexagon shape to be driven by a similarly shaped socket of a suitable anchor inserter or screwdriver.

It will further be appreciated that the screws 20 and/or the crimping process described may similarly be used in other surgical procedures. For example, the screws and/or the crimping may be used in a bladder neck suspension procedure for treatment of urinary stress incontinence, as described in U.S. Pat. No. 5,520,700 and U.S. patent application Ser. No. 08/572,682 and 08/804,172, as well as in other procedures known in the art. The inventive principle of these screws, wherein proximal portion 26 is made to grasp suture 32 and to assume a drivable polygonal shape in a single crimping operation, may also be applied advantageously to many various types of surgical screws and anchors which are known in the art.

An example of a suitable anchor inserter or screwdriver is shown in FIG. 4A. FIG. 4A is an illustration of a J-shaped, nonlinear, motorized screwdriver 40, for driving a screw 20, in accordance with the present invention into the bone. Screwdriver 40 may be a disposable, single-use device or, alternatively, may be sterilizable and reusable. It includes a handle 42 containing an electric motor 44 which is driven by batteries 46 in response to activation of a trigger 48. The rotating axle of motor 44 is coupled via a transmission 50 to the proximal end of a flexible, nonlinear drive shaft 52, which passes through a bore 53 of the screwdriver. An alternative is a rigid drive shaft with two nonlinear (90°) transmissions. A torque sensor mechanism 58 is coupled to transmission 50 and activates an indicator lamp 62 in response to a change in the torque of the transmission, as will be described below. The transmission 50 and nonlinear drive shaft 52 convert the rotary motion of the axle of motor 44 to a drive torque for a socket, matching in shape to the rear or proximal portion 26 of screw 20, located at the distal tip of the screwdriver.

The distal end of drive shaft 52 is secured to and turns a hex-shaped socket 54, which is shaped and sized to receive and firmly hold the crimped, hexagonal proximal portion 26 of screw 20. Socket 54 is radially surrounded by a pressure-retractable anchor tip protector 57, which prevents the sharp tip of screw 20 from accidentally injuring tissue during its insertion into the patient's mouth, as will be described below. Preferably, when screw 20 is critically placed into socket 54, suture 32 (attached to the screw by the crimping procedure) is drawn axially through a section of the bore 53 and protrudes out through a small hole 55 in a distal bend of the device. Further preferably, the protruding portion of the suture is protected by a sleeve 59.

FIG. 4B is an enlarged, cross-sectional illustration showing details of the distal end of screwdriver 40 and the screw 20 held thereby, as the screw is driven into a bone 60. Socket 54 is driven by rotation of drive shaft 52. Socket 54 rotates screw 20 to drill a hole 64 in bone 60. Because socket 54 has an outer radial diameter that is smaller that the outside diameter of thread 24 of screw 20, distal portion 22 of screw 20 will continue to bore into bone 60 until the entire proximal portion 26 is recessed below an outer surface 66 of the bone. Meanwhile, anchor tip protector 57 retracts due to pressure of screwdriver 40 against the surface of bone 60.

After hole 64 has reached a desired depth and the screw 20 located below the surface of the bones, however, a shoulder 56 at the distal end of the screwdriver will abut bone surface 66. At this point, the socket and screw 20 will continue to rotate and the screw will move further into the bone, at least bore a short distance further, until the screw has bored far enough so that hexagonal proximal portion 26 of the screw moves out of the grip of the socket. Torque sensor 58 senses that screw 20 is then disengaged from socket 54, due to the reduced torque exerted by drive shaft 52, and lights lamp 62 or, alternatively or additionally, activates an audible alarm to notify a physician operating screwdriver 40 that screw 20 is in place.

In addition to the shoulder 56, to further monitor the degree of screw penetration, a depth measurement is possible, if desired. An axially movable element, such as a pin, can be provided which protrudes near the drive socket and is pushed backwardly or recessed as the screw enters and moves through the bone. Once the screw reaches a predetermined depth, and the pin has therefore been pushed backward or recessed a predetermined distance, a mechanical or electrical indicator can be triggered, which lights lamp 62 and/or activates an audible alarm or the like to notify the physician.

Additionally, a bone contact indicator 140 (see FIG. 13) can be provided to the anchor inserter/screwdriver device. This element, shown in FIG. 13, is added to the screwdriver or anchor inserter at a location above socket or shoulder 143, i.e. between the portion of the screwdriver which cannot enter the bone and the portion of the socket which enters the bone itself. Bone contact indicator 140 consists of a washer 146 with protruding, radially-spaced spikes 152. As the screw 20 is being inserted into the bone of the patient, washer 146 will come into contact with the surface of the bone when hole 64 reaches its desired depth. Upon contact of washer 146 with the bone, spikes or rough surfaces 152 of washer 146 provide friction between the washer and the bone's surface which restricts or prevents the washer's further rotation. Due to the continued rotation of socket 54 of the screwdriver, however, spiral bump 158 of washer 146 will rotate into contact with spiral ridge or bump 160 of the screwdriver. At this point, the continued rotation of the socket with respect to washer 146 and the pressure due to contact of washer 146 with the bone, will result in continued periodic axial "jumping" of the washer 146 relative to the socket 143, causing a repeated noise, i.e. an audible "clicking" or "knocking". The screwdriver or inserter will also jump somewhat and the torque will vary in a periodic manner. The periodic nature of the effect, including the clicking and the vibration, will be easily heard and/or felt by the user. This effect can also be felt by the load on the motor- an electronic torque sensor and indicator as described above could be used to sense this periodic variation in torque. Upon hearing and/or feeling this effect, the physician will be able to tell that the bone contact indicator has now come into contact with the bone, and the screw has been completely inserted to its necessary depth.

With respect to those aspects of the procedure which require suture passers, several devices are currently known in the art such as Deschamps or Hurd suture passers. However, these devices are difficult to use for a variety of reasons. There is very limited room to maneuver these needles to penetrate the tongue, due to the dimensions and configuration of the mouth and these particular prior art devices. If there is 20 mm, for example, between the holes in the base of the tongue, then the needle must be at a minimum, 20 mm in length to extend between the two holes. However, at the same time, before penetration, that 20 mm needle must fit behind the base of the tongue. This can be difficult. Second, penetration of the tongue is difficult with a needle. In the procedures described, the physician is pushing against this soft tissue from a distance without any rigidity or resistance against which to press. Third, the suture passer must pass through the first hole in the tongue and exit though the second hole. This can be difficult and may require several tries until the second hole is located.

Figure 15A:
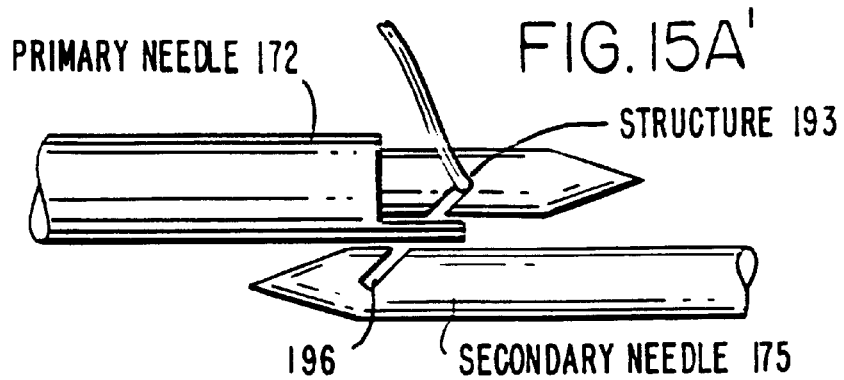
FIGS. 15A and 15B are plan views of the positioning of the primary needle and secondary needle of the suture passer of FIG. 14. The suture passer is provided with slanted slots in the needles to allow sutures to be transferred from the primary needle to the secondary needle, as shown in FIG. 14A. Both the open position of the needles, and the closed position are shown in FIG. 15B.
Figure 15A:
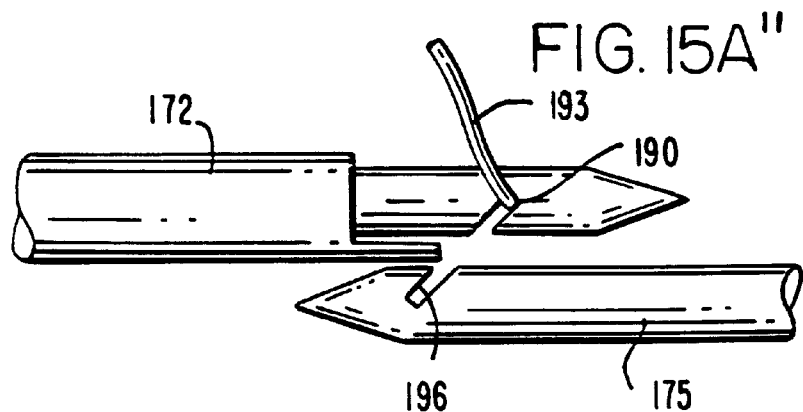
Figure 15:
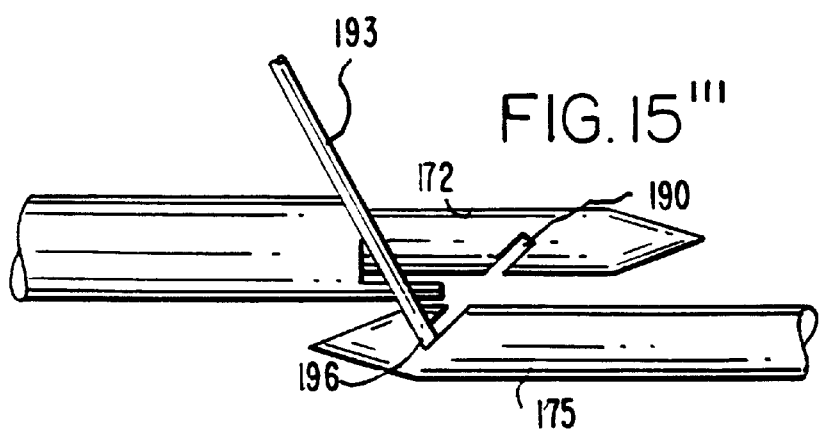

To address these problems, a novel suture passer 165 is provided, as shown in FIGS. 14 and 15. Suture passer 165 has handles 167 and 168 connected to primary needle 172 and secondary needle 175, respectively. The handles allow for relative rotation of the primary needle with respect to the secondary needle against the bias of a spring tending to open the two needles away from one another. The shaft 181 connected to the handle 168 for the secondary needle 175 passes through a pair of openings in ears 180 and 182 of the shaft 183 of the primary needle 172. The handles can be moved toward one another by one hand, which causes rotation of the shafts 181 and 183 with respect to one another, thereby closing or bringing together apart needles 172 and 175.

The suture passer is specifically designed and adapted for use in the disclosed tongue suspension procedures. During the procedure, the suture passer is placed in an open configuration, to spread primary needle 172 and secondary needle 175 apart, as shown in FIG. 15. The primary needle 172 is then inserted into the first hole in the tongue, while secondary needle 175 is inserted into the second hole in the tongue at the same time. The suture passer handles are then released to move the suture passer into the closed position shown in FIGS. 14 and 15. When the suture passer is moved into the closed position, the two needles are closed together to meet in the middle of the tongue.

As shown in FIG. 15B, upon moving the suture passer into the closed position, the two needles automatically move together to contact within the tongue and between the two holes. (When closed, as discussed with reference to FIG. 15A, the suture can easily be moved from the primary needle 172 to the secondary needle 175). The scissor-like mechanism of this suture passer ensures that the needles properly contact at a single point when the suture passer is placed into the closed configuration. Initially, before inserting the needles into the holes of the tongue, the suture is threaded into primary needle 172, while the secondary needle remains empty. Upon closing the two needles together, the two needles contact each other, and the suture is passed from the primary needle to the secondary needle.

As shown in FIG. 15A, the suture 193 is initially held in the primary needle 172 using an appropriate mechanism. Any of the mechanisms described hereafter for holding a suture can be utilized for holding the suture 193 in the primary needle 172. (See FIGS. 10–11B) These mechanisms can also be used for subsequently holding suture in the secondary needle 175.

Primary needle 172 has a slanted slot 190 in which the suture rests at the outset. Similarly, secondary needle 175 has a slanted slot 196. As the suture is pulled, it slides along the slanted slot 190 in primary needle 172 to slanted slot 196 of secondary needle 175. A small tug can therefore be used to slide the suture from the primary to the secondary needle. This provides an efficient means for transferring the suture from one needle to the next.

Once the suture has been transferred from the primary needle 172 to the secondary needle 175, the suture passer can then be moved into the open position, thus drawing the secondary needle, and the suture attached thereto, through the tongue and out through the second hole. Thus, by using two needles (instead of a single needle), the necessary needle size can be significantly reduced, and the ease of manipulation in the mouth can be significantly improved, since each needle only needs to extend halfway through the tongue, instead of the entire distance. Similarly, the simultaneous insertion design using two needles minimizes the difficulty of threading the suture passer through the tongue. The fact that the two needles are pressing in against the tongue towards a common intersection point also provide the necessary counterforce and resistance against each other to facilitate threading the needles through the tongue.

Another improved suture passer is shown in FIGS. 16A and 16B. This suture passer 200 provides the benefit of being capable of bending or looping inside the tongue. Suture passer 200 consists of a straight tube 210 with a lumen which holds rod 217. Although rod 217 normally has a curved shape (i.e. its ends form a semicircle), rod 217 is sufficiently resilient such that it can be forced into a straight shape when placed into the straight tube 210. One possible material for fabrication of the rod 217 is a shape memory metal or superelastic alloy which, due to the known properties of those alloys, can be induced to change shape in response to changes in temperature and/or applied stress.

Tube 210 can be pressed into the tongue until it reaches a point at or near the tongue's base. Rod 217 can then be pressed forward until it contacts the tube or until it forms a semicircle.

In the case where rod 217 contacts tube 210, the suture loop can be formed by one of two approaches. In a first approach, the suture can be resting in or on tube 210 to be grabbed by rod 217 when it is retracted back into tube 210. In a second approach, the suture can be carried by rod 217, which releases it when it contacts tube 210. In either approach, the suture is then grabbed using a different needle, and is then pulled out of the tongue.

In the case where rod 217 forms a semicircle, rod 217 may itself be provided with a lumen holding a normally straight needle 223 inside the rod. After rod 217 forms a semicircle in the tongue, the needle 223 can be pushed through the rod's lumen until exiting the tongue near the entrance hole for tube 210. Instead of a lumen, the rod 217 can also be constructed of two halves slit along the length of the rod, with a groove down the middle. These two halves can be joined at the beginning, end, or intermittently along the length of the rod.

Figure 11B:
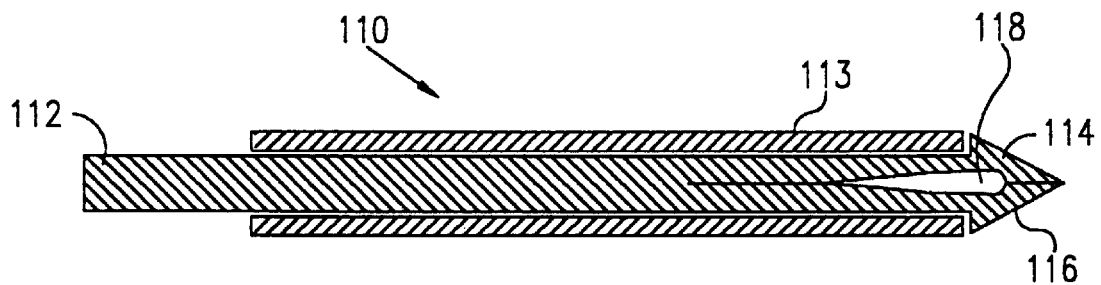

In addition, two devices are shown in FIGS. 10–11 for holding the suture in place (particularly in connection with the procedure of FIGS. 9A–9E). These devices can be used in conjunction with the new suture passers described herein or in conjunction with the suture passers of the prior art. FIG. 10 is a sectional illustration showing a suture passer 100. For the sake of clarity of illustration, FIG. 10, as well as FIGS. 11A and 11B, are not drawn to scale. Suture passer 100 comprises an elongate shaft 102, held in a generally cylindrical sleeve 104, such that the shaft can move axially or longitudinally within the sleeve. Shaft 102 includes a head 106 at a distal end of the shaft, for penetrating through tongue 76, and an eye 108 adjacent to head 106.

In order to pass a suture through tongue 76 (or through other tissue), the suture is inserted through side opening 109 of the shaft 102 and into eye 108, while shaft 102 is held in the open position relative to sleeve 104, as shown in FIG. 10. The shaft is then pulled proximally (to the left in FIG. 10 or the sleeve moved to the right with respect to the head of the shaft) through sleeve 104, until at least the side opening 109 is within the shaft 102. This prevents the suture from being accidentally removed. Alternatively, the rear of head 106 meets and abuts the distal end of the sleeve, whereupon the suture is grasped firmly and retained within eye 108. A recess or shot can be provided to accommodate the thickness of the suture. In this configuration, suture passer 100 is inserted through the tongue, until head 106 emerges posteriorly from the tongue in a desired location. Shaft 102 is then pushed distally through sleeve 104 to release the suture in position, and the suture passer is withdrawn from the tongue.

FIGS. 11A and 11B are schematic, cross-sectional illustrations showing another version of a suture passer 110, in respective open and closed configurations. Suture passer 110 is used in a manner substantially similar to that described above with reference to suture passer 100.

Suture passer 110 comprises a shaft 112 having bifurcated piercing, yet resilient, half-arrow-shaped heads 114 and 116, with a gap 118 between the heads. Shaft 112 is movably held within a cylindrical sleeve 113. As shown in FIG. 11A, to insert a suture into suture passer 110, shaft 112 is pushed distally through sleeve 113, so that heads 114 and 116 separate by their material resiliency, and gap 118 opens. The suture is inserted in gap 118, and shaft 112 is then drawn back proximally, as shown in FIG. 11B, so that heads 114 and 116 are pulled together, within the sleeve 113, thereby closing gap 118 and holding the suture fly. The two half-arrow-shaped heads, 114 and 116, when held together, form a single piercing point. Once the suture has been passed to a desired position, suture passer 110 is returned to the open configuration of FIG. 11A, and the suture is released.

An additional suture passer 208 is shown in FIG. 17. Suture passer 208 is constructed of an outer tube 214 having a lumen 215 and a slot 221 in the outer tube 214 wall. A rod 226 of a diameter slightly less than that of lumen 215 is inserted into, and slides within the outer tube 214 lumen 215. Suture 229 is inserted into suture passer 208 by threading an end of suture 229 through slot 221 to rest within lumen 215. By sliding rod 226 along lumen 215, rod 226 can be pressed to bear against suture 229, to wedge the suture 229 against the inner wall of lumen 215. When release of suture 229 from suture passer 208 is desired, the rod 226 can be slid out backward away from contact with suture 229, allowing the suture 229 to be easily removed.

Although in the above embodiments, the tongue's suspension is preferably carried out using bone screws 20 and/or 80 and screwdriver 40 and/or suture passer 100 or 110, or 208, or so forth, other tools could be used, if necessary. For example, other suitable bone anchor and insertion devices may be used for securing sutures 32 to mandible 72. Fixtures and screws that are driven into the mandible for setting fractures thereof and surgical tools used to drive such screws can be adapted for use in other preferred embodiments of the invention. In still other preferred embodiments of the present invention, sutures 32 may be fixed to mandible 72, using devices and methods described in the above-mentioned Israeli Patent Application No. 119151, incorporated herein by reference. Furthermore, such screws, anchors, sutures and/or other fixtures may be fastened to the mandible at any suitable location, not only near the midline or the ends as described above.

Having described this invention with regard to specific embodiments, it is to be understood that the description is not meant as a limitation since further modifications may suggest themselves or be apparent to those skilled in the art. The application is intended to cover all such modifications and variations as fall within the scope of the appended claims.

What is claimed is:

1. A method for treatment of airway obstruction, comprising:

providing a self tapping bone anchor which is sized for insertion into the mandible of a human patient, said bone anchor having attached suture;

inserting said bone anchor into a bone in the mouth of a patient using an anchor insertion device, said anchor insertion device having a distal portion for holding said anchor, said anchor insertion device being of a non-linear configuration such that said distal portion of said device can be inserted into the mouth of the patient for insertion of the bone anchor into the mandible of the patient, said anchor insertion device further having an activating trigger located outside of the patient's mouth; and, suspending the tongue of the patient using said suture, to prevent the tongue from obstructing the patient's airway.

2. A method as claimed in claim 1, further comprising the step of passing said suture through the tongue of the patient.

3. A method as claimed in claim 2, wherein said suture is passed through the tongue of the patient using a suture passer.

4. A method for treatment of airway obstruction, comprising:
providing a bone anchor, said bone anchor having suture attached thereto;
inserting said bone anchor into a bone in the mouth of a patient; and,
suspending the tongue of the patient using said suture to prevent the tongue from obstructing the patient's airway.

5. A method as claimed in claim 4, wherein said bone anchor is inserted using a bone anchor inserter.

6. A method as claimed in claim 5, wherein said bone anchor inserter further comprises shut-off indicating means associated with said bone anchor inserter to detect a change in torque during insertion of said bone anchor into bone.

7. A method as claimed in claim 5, wherein said bone anchor inserter further comprises suture protective means to protect said suture as said bone anchor is driven into bone.

8. A method as claimed in claim 5, wherein said bone screw anchor inserter comprises torque sensing means for detecting the decrease in torque acting on a bone anchor as it is inserted into bone.

9. A method as claimed in claim 8, wherein said torque sensing means is connected to a visual light which illuminates upon the decrease of said torque acting by said bone anchor inserter on a bone anchor as it is inserted into bone.

10. A method as claimed in claim 8, wherein said torque sensing means provides the user of said bone anchor inserter with an indication that said torque acting on said bone anchor by said bone anchor inserter has decreased.

11. A method as claimed in claim 10, wherein said indication is tactile.

12. A method as claimed in claim 10, wherein said indication is audible.

13. A method as claimed in claim 10, wherein said indication is visual.

14. A method as claimed in claim 10, wherein said indication is accomplished by the combination of a spiral ramp located at the driving end of the bone anchor inserter which causes a washer with a mating head and imbedding spikes to ride thereover such that the spikes embed into the surface of the bone upon maximum desired insertion of said bone anchor into bone, and the torque of said imbedding causes said washer to glide over and then slip back onto said ramp.

15. A method as claimed in claim 5, wherein said bone anchor inserter comprises a driving end, and wherein said driving end is provided with a retractable pin element which contacts and is forced backwardly as said bone anchor is inserted into bone until said pin element causes an electrical shut-off of said bone anchor inserter.

16. A method as claimed in claim 4, wherein said bone anchor is a self tapping bone screw anchor comprising a distal bone-piercing tip portion and a proximal portion of smaller diameter than said tip portion, said proximal portion comprising an external spiral thread, said proximal portion further comprising a rearwardly directed suture holding hole for receiving and securing said suture thereto.

17. A method as claimed in claim 4, wherein said bone anchor is a self tapping bone screw anchor comprising a distal bone-piercing tip portion and a proximal portion of smaller diameter than said tip portion, said proximal portion comprising an external spiral thread, and wherein said proximal portion is crimped onto said suture to simnultaneously secure said suture and form said proximal portion into a driving shape.

18. A method as claimed in claim 17, wherein said driving shape is non-circular.

19. A method as claimed in claim 17, wherein said proximal portion is crimped to form a hexagonal shape.

20. A method as claimed in claim 4, wherein said bone anchor comprises a bone-boring tip and a rearwardly-located proximal body portion, said body portion being provided with screw threads for facilitating insertion of said bone anchor into bone; said body portion having a rear-end portion of a non-circular shape;
and wherein said bone anchor is inserted using a bone anchor inserter, said bone anchor inserter comprising a rotatable driving socket of a shape corresponding to said non-circular shape of said rear-end portion of said body portion; the diameter of said driving socket being less than the maximum diameter of said screw threads of said bone anchor.

21. A method as claimed in claim 20, wherein said bone anchor inserter further comprises shut-off indicating means associated with said bone anchor inserter to detect a change in torque during insertion of said bone anchor into bone.

22. A method as claimed in claim 20, further comprising bone contact means associated with said bone anchor inserter and said driving socket, said bone contact means being of a greater diameter than the maximum diameter of said screw threads of said bone anchor.

23. A method as claimed in claim 20, wherein said bone anchor inserter further comprises suture protective means to protect said suture as said bone anchor is driven into bone.

24. A method as claimed in claim 4, wherein said suture is threaded through the patient's tongue using a suture passer, said suture passer comprising:
a) a body defining a bore passing therethrough, said body having an inner wall; and,
b) a rod portion, said rod portion located in said hollow body, said body being provided with an opening for threading of a suture into said body, said rod axially movable within said body to slide within said body past said opening to secure a suture into said body by wedging the suture between said rod and said inner wall.

25. A method as claimed in claim 24, wherein said suture passer further comprises a piercing tip.

26. A method as claimed in claim 24, wherein said rod of said suture passer is provided with a resilient forward end which when extended from said hollow body splits outwardly to provided a longitudinal forward facing opening, said opening closing when said forward end is retracted into said rod.

27. A method as claimed in claim 26, wherein said forward end of said rod splits into sections forming, when retracted into said rod, said piercing tip.

28. A method as claimed in claim 4, wherein said suture is attached to an implantable electrode for implantation within a patient and capable of activating a nerve for controlling the position of the tongue; and further comprising the step of implanting an induction coil in the patient in electrical connection with said electrode.

29. A method as claimed in claim 28, further comprising the step of providing an externally positionable driving coil for location outside the patient, and drivable with appropriate current to create a magnetic field and induced current in said induction coil for delivering energy to said induction coil such that said induction coil can deliver energy to said implantable electrode to activate a patient's nerve.

30. A method as claimed in claim 29, further comprising the step of providing an electric current controller for creating and controlling said magnetic field in said driving coil.

31. A method as claimed in claim 30, further comprising an external sensor in electrical connection with said controller, said sensor being capable of detecting a characteristic of airway obstruction, and when so detecting, providing an electrical signal to said controller to activate said driving coil.

32. A method as claimed in claim 31, wherein said sensor comprises a microphone.

33. A method as claimed in claim 31, wherein said sensor is a chest motion sensor.

34. A method as claimed in claim 31, wherein said sensor is an airflow sensor.

35. A method as claimed in claim 30, further comprising a sensor in electrical connection with said controller, said sensor being capable of detecting the position of the tongue as a function of muscle tone of the same and providing an electrical signal to said controller to activate said driving coil.

36. A method as claimed in claim 35 wherein said sensor is a piezoelectric element.

37. A method, comprising:
  suspending the base of a patient's tongue, said suspension being conducted by attaching said base of the tongue to a bone using sutures.

38. A method as claimed in claim 37, wherein said suture is threaded through the patient's tongue using a suture passer, said suture passer comprising:
  a) a body defining a bore passing therethrough, said body having an inner wall; and,
  b) a rod portion, said rod portion located in said hollow body, said body being provided with an opening for threading of a suture into said body, said rod axially movable within said body to slide within said body past said opening to secure a suture into said body by wedging the suture between said rod and said inner wall.

39. A method as claimed in claim 38, wherein said suture passer further comprises a piercing tip.

40. A method as claimed in claim 37, wherein said suture is attached to an implantable electrode for implantation within a patient and capable of activating a nerve for controlling the position of the tongue; and further comprising the step of implanting an induction coil in the patient in electrical connection with said electrode.

41. A method as claimed in claim 40, further comprising the step of providing an externally positionable driving coil for location outside the patient, and drivable with appropriate current to create a magnetic field and induced current in said induction coil, for delivering energy to said induction coil such that said induction coil can deliver energy to said implantable electrode to activate a patient's nerve.

42. A method as claimed in claim 41, further comprising the step of providing an electric current controller for creating and controlling said magnetic field in said driving coil.

43. A method as claimed in claim 42, further comprising an external sensor in electrical connection with said controller, said sensor being capable of detecting a characteristic of airway obstruction, and when so detecting, providing an electrical signal to said controller to activate said driving coil.

44. A method as claimed in claim 43, wherein said sensor comprises a microphone.

45. A method as claimed in claim 43, wherein said sensor is a chest motion sensor.

46. A method as claimed in claim 43, wherein said sensor is an airflow sensor.

47. A method as claimed in claim 42, further comprising a sensor in electrical connection with said controller, said sensor being capable of detecting the position of the tongue as a function of muscle tone of the same and providing an electrical signal to said controller to activate said driving coil.

48. A method as claimed in claim 47, wherein said sensor is a piezoelectric element.

49. A method as claimed in claim 37, wherein said suture is threaded through the patient's tongue using a suture passer, said suture passer comprising a pair of rods each having a handle end and an arc-shaped piercing tip facing one another, each tip having a suture gasping segment which, when the tips are in an adjacent position to one another, allows suture to be transferred from one piercing tip to the other, said rods and said piercing tips being rotatable about one another by squeezing together or release of said handles, such that said piercing tips penetrate a tissue from both sides and suture is passed through the hole formed by said piercing tips.

50. A method as claimed in claim 49, wherein said handles are spring-biased such that said piercing tips are in said adjacent position.

51. A method as claimed in claim 49, wherein one of said rods is provided with a rotation bearing for the other of said rods.

52. A method as claimed in claim 49, wherein suture holding and release means are provided to at least one of said piercing tips.

53. A method as claimed in claim 49, wherein said piercing tips are provided with opposed and mating slots to facilitate the selective transfer of suture from one of said piercing tips to the other.

54. A method as claimed in claim 53, wherein said slots are angled with respect to the longitudinal axis of said piercing tips.

55. A method as claimed in claim 37, wherein said suture is inserted using a suture passer, said suture passer comprising a straight tube defining a lumen, and comprising a rod reciprocable within said lumen, said rod being formed from an elastic material such that when retracted into said tube it is substantially straight and such that when projected forwardly from said tube the portion of said rod projecting from tube bends to form a circular configuration, said rod having suture holding and release means.

56. A method as claimed in claim 55, wherein said rod is formed with a second lumen and a tissue drilling needle passing through said second lumen.

57. A method as claimed in claim 56, wherein said suture holding and release means cooperates with said tissue drilling needle.

* * * * *